United States Patent
Keesee et al.

(10) Patent No.: US 6,218,131 B1
(45) Date of Patent: *Apr. 17, 2001

(54) MATERIALS AND METHODS FOR DETECTION OF BREAST CANCER

(75) Inventors: Susan K. Keesee, Harvard; Robert Obar, Walpole; Ying-Jye Wu, Framingham, all of MA (US)

(73) Assignee: Matritech, Inc., Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/944,604

(22) Filed: Oct. 6, 1997

Related U.S. Application Data

(63) Continuation-in-part of application No. 08/658,639, filed on Jun. 5, 1996, now Pat. No. 5,914,238.

(51) Int. Cl.$^7$ .................................................. G01N 33/574
(52) U.S. Cl. ..................... 435/7.23; 530/324; 530/326; 530/327; 530/328; 530/329; 530/387.7; 530/387.9
(58) Field of Search .......................... 435/7.23; 530/324, 530/326, 327, 328, 329, 387.7, 387.9

(56) References Cited

U.S. PATENT DOCUMENTS

| | | | |
|---|---|---|---|
| 4,704,692 | 11/1987 | Ladner ................................. | 364/496 |
| 4,775,620 | 10/1988 | Cardiff et al. ........................... | 435/7 |
| 4,882,268 | 11/1989 | Penman et al. .......................... | 435/5 |
| 4,885,236 | 12/1989 | Penman et al. .......................... | 435/6 |
| 4,946,778 | 8/1990 | Ladner et al. .......................... | 435/69 |
| 5,091,513 | 2/1992 | Huston et al. ....................... | 530/387 |
| 5,132,405 | 7/1992 | Huston et al. ....................... | 530/387 |

FOREIGN PATENT DOCUMENTS

| | | |
|---|---|---|
| WO93/09437 | 5/1993 | (WO) . |
| WO94/12881 | 6/1994 | (WO) . |
| WO94/18222 | 8/1994 | (WO) . |
| WO95/16919 | 6/1995 | (WO) . |
| WO97/12975 | 4/1997 | (WO) . |

OTHER PUBLICATIONS

Laue et al. (1990) "Determination of Size, Molecular Weight, and Presence of Subunits," *Methods in Enzymology*, 182:566–587.
Sambrook et al. (1989) "SDS–Polyacrylamide Gel Electrophoresis of Proteins," *Molecular Cloning, A Laboratory Manual*, 18.47–18.48.
Anderson et al. (1993) "A Cyclophilin–related Protein Involved in the function of Natural Killer Cells" Proc. Nat'l. Acad. Sci., USA 90:542–546.
Bergsma et al. (1991) "The Cyclophilin Multigene Family of Peptidly–Prolyl Isomerases: Characterization of Three Separate Human Isoforms" J. Biol. Chem. 266(34):23204–23214.
Bohm et al. (1989) "The Growth–related Protein P23 of the Ehrlich Ascites Tumor: Translational Control, Cloning and Primary Structure" Biochem. Int'l. 19(2):277–286.
Urlaub, et al. (1980) "Isolation of Chinese Hamster Cell Mutants Deficient in Dihydrofolate Reductase Activity," Proc. Nat'l Acad. Sci., USA 77(7):4216–4222.
Chitpatima et al.(1988) "Nucleotide Sequence of a Major Messenger RNA for a 21 Kilodalton Polypeptide that is Under Translational Control in Mouse Tumor Cells," Nucleic Acids Research 16(5):2350.
Ciejek et al. (1982)."Actively Transcribed Genes are Associated with the Nuclear Matrix" Nature 306:607–609.
Durfee et al. (1993) "The Retinoblastoma Protein Associates with the Protein Phosphatase Type 1 Catalytic Subunit" Genes and Development 7:555–569.
Fey et al. (1988) "Nuclear Matrix Proteins Reflect Cell Type or Origin in Cultured Human Cells" Proc. Nat'l. Acad. Sci. USA 85:121–125.
Ford et al. (1995) "The Genetics of Breast and Ovarian Cancer" British J. Cancer, 72:805–812.
Galat (1993) "Peptidylproline cis–trans–isomerases: Immunophilins" Eur. J. Biochem 216:689–707.
Getzenberg et al. (1991) "Identification of Nuclear Matrix Proteins in the Cancer and Normal Rat Prostate[1]" Cancer Res. 51:6514–6520.
Getzenberg et al. (1990) "The Tissue Matrix: Cell Dynamics and Hormone Action," Endocrine. Rev. 11(3):399–417.
Gross et al. (1989) "cDNA Sequence Coding for a Translationally Controlled Human Tumor Protein" Nucleic Acids Research 17(20):8367.
Hacker et al. (1993) "Immunophilins: Structure–function Relationship and Possible Role in Microbial Pathogenicity" Molecular Microbiology 10(3):445–456.
Harding (1991) "Structural and Functional Features of the Peptidly Prolyl Cis–Trans Isomerase, Cyclophilin" Pharmacotherapy 11(6):142S–148S.
Ji et al. (1994) "Two–dimensional Electrophoretic Analysis of Proteins Express by Normal and Cancerous Human Crypts: Application of Mass Spectrometry to Peptide–mass Fingerprinting" Electrophoresis 15:391–405.
Khanuja et al. (1993) "Nuclear Matrix Proteins in Normal and Breast Cancer Cells[1]" Cancer Res. 53:3394–3398.
Koletsky et al. (1986) "Cyclophilin: Distribution and Varian Properties in Normal and Neoplastic Tissues[1]" J. of Immunology, 137(3):1054–1059.
Kozaki et al. (1974) "Purification and Some Properties of Progenitor Toxins of Clostridium Botulinum Type B" Infection and Immunity, 10(4):750–756.

(List continued on next page.)

Primary Examiner—Donna C. Wortman
Assistant Examiner—Brenda G. Brumback
(74) Attorney, Agent, or Firm—Testa, Hurwitz & Thibeault, LLP

(57) ABSTRACT

Disclosed are proteins indicative of breast cancer and of other cancers, and methods for their detection. Methods of the invention provide an improvement in cancer detection assays, especially in breast cancer detection assays.

25 Claims, 8 Drawing Sheets

OTHER PUBLICATIONS

Malkin et al. (1990) "Germ Line p53 Mutations in a Familial Syndrome of Breast Cancer, Sarcomas, and Other Neoplasms" Science 250:1233–1238.

Miki et al. (1994) "A Strong Candidate for the Breast and Ovarian Cancer Susceptibility Gene BRCA1" Science 266:66–71.

Mortillaro et al. (1995) "Association of a Nuclear Matrix Cyclophilin with Splicing Factors" Journal of Cellular Biochemistry Supplement 0–(21B) Abstract No. J7–318.

Rasmussen et al. (1992) "Microsequences of 145 Proteins Recorded in the Two–dimensional Gel Protein Database of Normal Human Epidermal Keratinocytes," Electrophoresis 13:960–969.

Sanchez et al.(Feb., 1994)"Global Yeast Genome Expression Analyzed by 2–D Page After TCTP Homolog Gene (YKL312) Disruption," Experientia 50:A35 Abstract No. S10–19 from the 26th Annual Meeting of the Swiss Societies for Experimental Biology [USGEB/USSBE], Mar. 17–18, 1994.

Schaller et al. (Feb., 1994) "A Yeast Gene Homologous to the Mammalian Translationally Controlled Tumor Protein TCTP: Gene Disruption and Expression Studies" Experientia 50:A34 Abstract No. S10–16 from the 26th Annual Meeting of the Swiss Societies for Experimental Biology [USGEB/USSBE], Mar. 17–18, 1994.

Stamnes et al. (1992) "Cyclophilins: A New Family of Proteins Involved in Intracellular Folding" Trends in Cell Biol. 2:272–276.

Stuurman et al. (1990) "The Nuclear Matrix from Cells of Different Origin" J. Biol. Chem. 265:5460–5465.

Swift et al. (1991) "Incidence of Cancer in 161 Families Affected by Ataxia–Telangiectasia" N. Engl. J. Med., 325(26):1831–1836.

Ward et al. (1990) "Development of a Database of Amino Acid Sequences for Human Colon Carcinoma Proteins Separated by Two–dimensional Polyacrylamide Gel Electrophoresis" Electrophoresis 11:883–891.

Wooster et al. (1994) "Localization of a Breast Cancer Susceptibility Gene, BRCA2, to Chromosome 13q12–13" Science 265:2088–2090.

Wrana et al. (1992) "TGFβ Signals Through a Heteromeric Protein Kinase Receptor Complex" Cell 71:1003–1014.

Wu et al. (1995) "Nup358, A Cytoplasmically Exposed Nucleoporin with Peptide Repeats, Ran–GTP Binding Sites, Zinc Fingers, A Cyclophilin A Homologous Domain, and a Leucine–rich Region*" J. Biol. Chem. 270(23):14209–14213.

Naber, S., et al., Laboratory Investigation, "Annual Meeting Abstracts", vol. 64, No. 1, 2 pgs., Jan. 1991.

Multhaupt, H., et al., The Faseb Journal, "Abstracts Part II", vol. 6, No. 5, 2 pgs., Feb. 28, 1992.

Kallajoki et al., "Gel Electrophoretic Analysis of Nuclear Matrix Fractions Isolated from Different Human Cell Lines", Electrophoresis, vol. 15, No. 3–4, p. 520–8 (1994).

Wu et al., "Nuclear Matrix Proteins as Tumor Markers" J. Cell Biochem. vol. 21B, p. 126 (1995).

Pienta, K. et al., "Nuclear Matrix Proteins in Human Breast and Prostate Cancer Patients" J. Cell Biochem. vol. 21B, p. 125 (1995).

Laue et al. (1990) "Determination of Size, Molecular Weight, and Pressure of Subunits," *Methods in Enzymology*, 182:566–587.

Sambrook et al. (1989) "SDS–Polyacrylamide Gel Electrophoresis of Proteins," *Molecular Cloning, A Laboratory Manual*, 18.47–18.48.

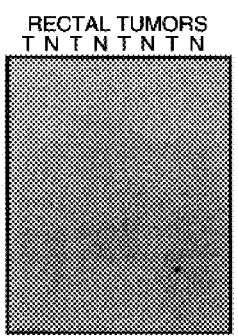
FIG. 4A — RECTAL TUMORS T N T N T N T N
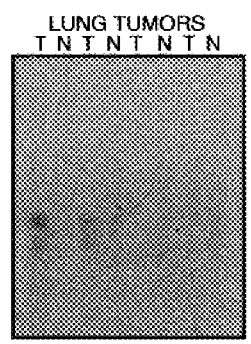
FIG. 4B — LUNG TUMORS T N T N T N T N
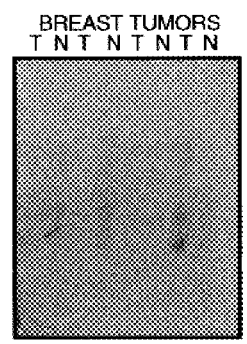
FIG. 4C — BREAST TUMORS T N T N T N T N
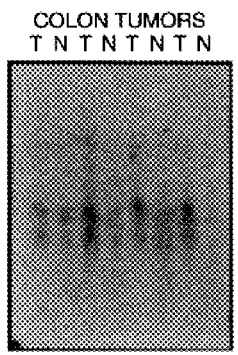
FIG. 4D — COLON TUMORS T N T N T N T N
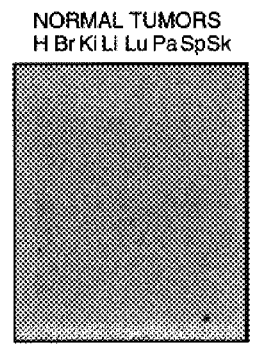
FIG. 4E — NORMAL TUMORS H Br Ki Li Lu Pa Sp Sk

MATERIALS AND METHODS FOR DETECTION OF BREAST CANCER

REFERENCE TO RELATED APPLICATIONS

This application is a continuation-in-part of U.S. Ser. No. 08/658,639, filed Jun. 5, 1996, now U.S. Pat. No. 5,914,238.

FIELD OF THE INVENTION

The present invention relates to materials and methods for the detection of breast cancer, including cellular markers indicative of the likelihood of the presence of breast cancer.

BACKGROUND OF THE INVENTION

Breast cancer is a leading cause of death in women. While the pathogenesis of breast cancer is unclear, transformation of normal breast epithelium to a malignant phenotype may be the result of genetic factors, especially in women under 30. Miki, et al., Science, 266: 66–71 (1994). However, it is likely that other, non-genetic factors also have a significant effect on the etiology of the disease. Regardless of its origin, breast cancer morbidity increases significantly if a lesion is not detected early in its progression. Thus, considerable effort has focused on the elucidation of early cellular events surrounding transformation in breast tissue. Such effort has led to the identification of several potential breast cancer markers. For example, alleles of the BRCA1 and BRCA2 genes have been linked to hereditary and early-onset breast cancer. Wooster, et al., Science, 265: 2088–2090 (1994). The wild-type BRCA1 allele encodes a tumor supressor protein. Deletions and/or other alterations in that allele have been linked to transformation of breast epithelium. Accordingly, detection of mutated BRCA1 alleles or their gene products has been proposed as a means for detecting breast, as well as ovarian, cancers. Miki, et al., supra. However, BRCA1 is limited as a cancer marker because BRCA1 mutations fail to account for the majority of breast cancers. Ford, et al., British J. Cancer, 72: 805–812 (1995). Similarly, the BRCA2 gene, which has been linked to forms of hereditary breast cancer, accounts for only a small portion of total breast cancer cases. Ford, et al., supra.

Several other genes have been linked to breast cancer and may serve as markers for the disease, either directly or via their gene products. Such potential markers include the TP53 gene and its gene product, the p53 tumor supressor protein. Malkin, et al., Science, 250: 1233–1238 (1990). The loss of heterozygosity in genes such as the ataxia telangiectasia gene has also been linked to a high risk of developing breast cancer. Swift, et al., N. Engl. J. Med., 325: 1831–1836 (1991). A problem associated with many of the markers proposed to date is that the oncogenic phenotype is often the result of a gene deletion, thus requiring detection of the absence of the wild-type form as a predictor of transformation.

Of interest to the present invention are reports that the protein content of the nuclear matrix in breast epithelia may provide a marker of cellular growth and gene expression in those cells. Khanuja, et al., Cancer Res., 53: 3394–3398 (1993). The nuclear matrix forms the superstructure of the cell nucleus and comprises multiple protein components that are not fully characterized. The nuclear matrix also provides the structural and functional organization of DNA. For example, the nuclear matrix allows DNA to form loop domains. Portions of DNA in such loop domains have been identified as regions comprising actively-transcribing genes. Ciejek, et al., Nature, 306: 607–609 (1982). Moreover, the organization of the nuclear matrix appears to be tissue-specific and has been associated with so-called transformation proteins in cancer cells. Getzenberg, et al., Cancer Res., 51: 6514–6520 (1991); Stuurman, et al., J. Biol. Chem., 265: 5460–5465 (1990).

Proteins and steroid hormones thought to be involved in transformation are associated with the nuclear matrix in certain cancer cells. Getzenberg, et al., Endocrinol. Rev., 11: 399–417 (1990). It has been suggested that changes in the composition or organization of nuclear matrix proteins may be useful as markers of growth and gene expression in breast tissue. Khanuja, et al., Cancer Res., 53: 3394–3398 (1994). However, Khanuja did not identify any specific proteins for use as cancer markers.

There is, therefore, a need in the art for specific, reliable markers that are differentially expressed in normal and transformed breast tissue and that may be useful in the diagnosis of breast cancer or in the prediction of its onset. Such markers and methods for their use are provided herein.

SUMMARY OF THE INVENTION

The invention provides materials and methods for diagnosis and detection of breast cancer in tissue or in body fluid. In a preferred embodiment, methods according to the invention comprise the step of detecting in a sample of tissue or body fluid the presence of a protein that is not normally expressed in non-transformed (i.e., noncancerous) breast cells. Such proteins are typically found in the nuclear matrix fraction of cells or cellular material isolated according to the method of Fey, et al. Proc. Nat'l. Acad. Sci. (USA), 85: 121–125 (1988), incorporated by reference herein. Accordingly, such proteins are alternatively referred to herein as breast cancer-associated proteins or breast cancer-associated nuclear matrix proteins. It is understood that, for purposes of the present invention, a breast cancer-associated protein, including a nuclear matrix protein, is one that is detectable in breast cancer cells and not detectable in non-cancerous cells and which can be isolated as described herein.

Methods of the invention may be performed on any relevant tissue or body fluid sample. In preferred embodiments, methods of the invention are carried out in breast tissue and preferably breast biopsy tissue. However, inventive methods are also useful in assays for metastasized breast cancer cells in other tissue or body fluid samples. Methods for detecting breast cancer-associated proteins in breast tissue may comprise exposing such tissue to an antibody directed against a target breast cancer-associated protein. The antibody may be polyclonal or monoclonal and may be detectably labeled for identification of antibody.

A detecting step according to the invention may comprise amplifying nucleic acid encoding a target breast cancer-associated protein using a polymerase chain reaction or a reverse-transcriptase polymerase chain reaction. Detection of products of the polymerase chain reaction may be accomplished using known techniques, including hybridization with nucleic acid probes complementary to the amplified sequence. A detecting step according to the present invention may also comprise using nucleic acid probes complementary to at least a portion of a DNA or RNA encoding a breast cancer-associated protein.

The present invention also provides proteins and protein fragments that are characteristic of breast cancer cells. Such proteins and protein fragments are useful in the detection and diagnosis of breast cancer as, for example, in the production of antibodies. The invention also provides nucleic acids encoding breast cancer-associated proteins. The nucleic acids themselves are contemplated as markers and may be detected in order to establish the presence of breast cancer or a predisposition therefor.

In a preferred embodiment, methods of the invention comprise the step of detecting these proteins and/or nucleotides. Specifically, methods of the invention comprise detecting a breast cancer-associated protein having an amino acid sequence selected from the group consisting of SEQ ID NO: 16, SEQ ID NO: 18, and SEQ ID NO: 20; and/or a nucleotide sequence selected from the group consisting of SEQ ID NO: 15, SEQ ID NO: 17, and SEQ ID NO: 19.

Breast cancer-associated proteins in a tissue or body fluid sample may be detected using any assay method available in the art. In one embodiment, the protein may be reacted with a binding moiety, such as an antibody, capable of specifically binding the protein being detected. Binding moieties, such as antibodies, may be designed using methods available in the art so that they interact specifically with the protein being detected. Optionally, a labeled binding moiety may be utilized. In such an embodiment, the sample is reacted with a labeled binding moiety capable of specifically binding the protein, such as a labeled antibody, to form a labeled complex of the binding moiety and the target protein being detected. Detection of the presence of the labeled complex then may provide an indication of the presence of a breast cancer in the individual being tested.

In another embodiment, one or more breast cancer-associated protein(s) in a sample may be detected by isolation from the sample and subsequent separation by two-dimensional gel electrophoresis to produce a characteristic two-dimensional gel electrophoresis pattern. The cancer cell gel electrophoresis pattern then may be compared with a standard pattern obtained from non-cancer cells. The standard may be obtained from a database of gel electrophoresis patterns.

In another embodiment, nucleic acid probes are designed using standard methods and are used to identify DNA or mRNA encoding breast cancer-associated protein. See, e.g., Maniatis et al., "Molecular Cloning: A Laboratory Manual," Cold Spring Harbor Press (1989).

In another embodiment, a nucleic acid molecule may be isolated that comprises a sequence capable of recognizing and being specifically bound by a breast cancer-associated protein. As used herein, the term "specifically bound" refers to a binding affinity of greater than about $10^5$ $M^{-1}$.

Nucleic acid in a sample may also be detected by, for example, a Southern blot analysis by reacting the sample with a labeled hybridization probe, wherein the probe is capable of hybridizing specifically with at least a portion of the target nucleic acid molecule. Therefore, detection of the target nucleic acid molecule in a sample can serve as an indicator of the presence of breast cancer in the patient being tested. A nucleic acid binding protein may also be used to detect nucleic acid encoding breast cancer-associated proteins.

Numerous additional aspects and advantages of the invention will become apparent upon consideration of the following detailed description thereof.

BRIEF DESCRIPTION OF THE DRAWINGS

FIG. 4 is a panel of several northern blots of human malignancies and a normal tissue sample. Each lane contains approximately 20 ug of total RNA from normal (N) or tumor (T) tissue, as indicated. All the blots were probed with a radio-labelled BC-8 specific nucleotide. The two bands at 1.6 and 1.8 kb represent the two mRNAs of BC-8, BC-8A (SEQ ID NO: 17) and BC-8B (SEQ ID NO: 19).

DETAILED DESCRIPTION OF THE INVENTION

Figure 1:
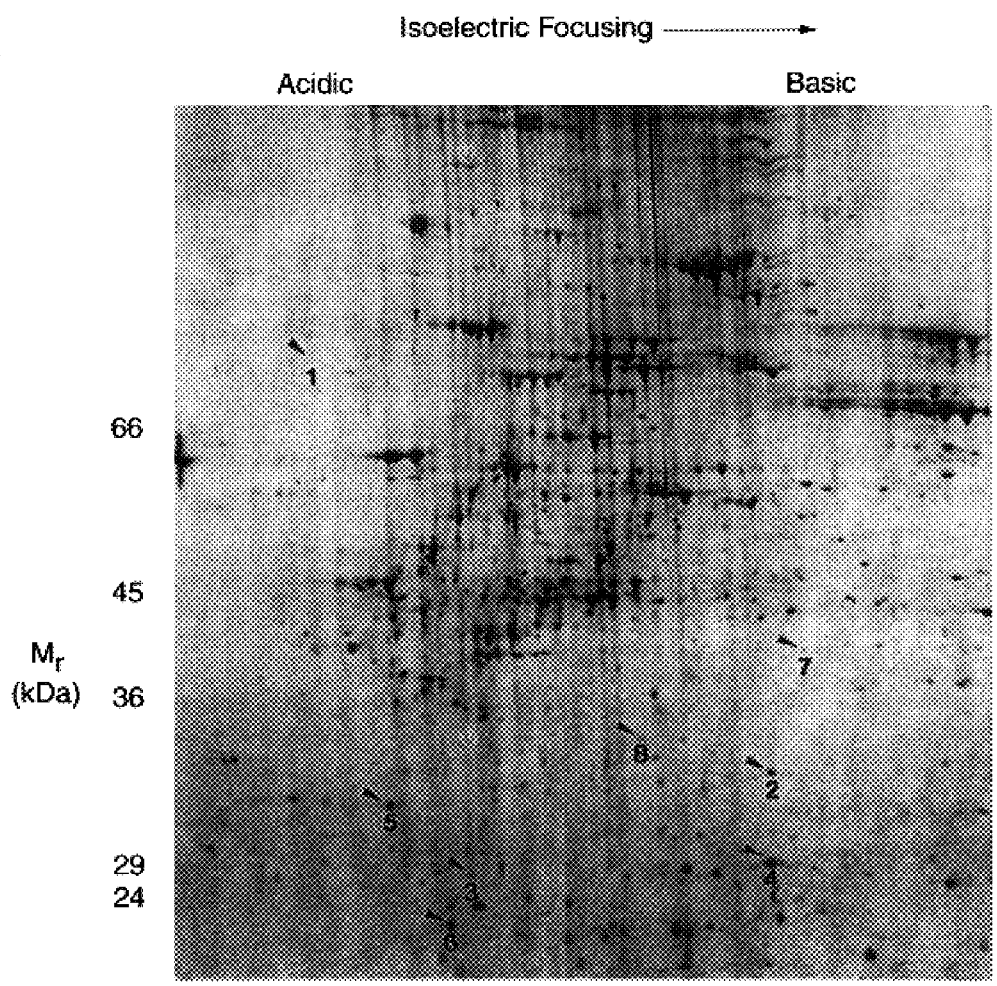
FIG. 1 is a two-dimensional gel electrophoresis pattern produced by nuclear matrix proteins obtained from a breast cancer tissue sample. Arrows 1 through 8 indicate proteins that are expressed in breast cancer tissue but not in normal tissue.

The present invention provides marker proteins, for example, nuclear matrix proteins, that are expressed in breast tumor cells but not in non-cancerous breast cells. The proteins, nucleic acids encoding them, and antibodies directed against them are useful in diagnostic assays and kits for early detection of breast cancer or the likelihood of onset of breast cancer. While detection of a single breast cancer-associated protein is sufficient to detect breast cancer cells, diagnostic methods according to the invention may include detection of more than one marker protein in a tissue or body fluid sample. Materials and methods of the invention provide consistent and reliable means for detection of a variety of breast cancers, including hereditary forms and induced forms.

Breast cancer protein markers may be isolated, purified, and characterized according to well-known techniques. Proteins are commonly characterized by their molecular weight and isoelectric point. Marker proteins according to the present invention and for use in methods of the invention are characterized as being detectable by two-dimensional gel electrophoresis of proteins isolated from breast cancer cells and not detectable by two-dimensional gel electrophoresis of proteins isolated from normal cells. For purposes of the present invention, the term normal cells refers to cells that are not cancerous or pre-cancerous.

Breast cancer-associated proteins may be isolated from a sample by any protein isolation method known to those skilled in the art, such as affinity chromatography. As used herein, "isolated" is understood to mean substantially free of undesired, contaminating proteinaceous material. For example, a breast cancer-associated nuclear matrix protein may be isolated from a cell sample using the methods for isolating nuclear matrix proteins disclosed in U.S. Pat. No. 4,885,236 and U.S. Pat. No. 4,882,268 (Such proteins are referred to therein as internal nuclear matrix proteins), the disclosures of which are incorporated by reference herein.

In such isolation procedures, mammalian cells are generally extracted with an extraction solution comprising protease inhibitors, RNase inhibitors, and a non-ionic detergent-salt solution at physiological pH and ionic strength, to extract proteins in the nucleus and cytoskeleton that are soluble in the extraction solution. The target proteins then are separated from the cytoskeleton remaining in the extracted cells by solubilizing the cytoskeleton proteins in a solution comprising protease inhibitors and a salt solution (such as 0.25 M $(NH_4)_2SO_4$) which does not dissolve the target proteins. The chromatin then is separated from the target proteins by digesting the insoluble material with DNase in a buffered solution containing protease inhibitors. The insoluble proteins then are dissolved in a solubilizing agent, such as 8 M urea plus protease inhibitors, and dialyzed into a physiological buffer comprising protease inhibitors, wherein the target proteins are soluble in the physiological buffer. Insoluble proteins are removed from the solution.

Marker proteins in a sample of tissue or body fluid may be detected in binding assays, wherein a binding partner for the marker protein is introduced into a sample suspected of containing the marker protein. In such an assay, the binding partner may be detectably labeled as, for example, with a radioisotopic or fluorescent marker. Labeled antibodies may be used in a similar manner in order to isolate selected marker proteins. Nucleic acids encoding marker proteins may be detected by using nucleic acid probes having a sequence complementary to at least a portion of the sequence encoding the marker protein. Techniques such as PCR and, in particular, reverse transcriptase PCR, are useful means for isolating nucleic acids encoding a marker protein. The following examples provide details of the isolation and characterization of breast cancer-associated proteins and methods for their use in the detection of breast cancer.

EXAMPLE 1

Isolation of Breast Cancer-Associated Proteins

Breast cancer marker proteins for use in the invention were first isolated by analysis of two-dimensional ("2-D") gel electrophoretic profiles. These proteins were then isolated and fully-sequenced by recombinant methods.

A. Isolation of Marker Proteins by 2-D Gel Electrophoresis.

Several different breast cancer marker proteins were isolated by comparison of 2-D gel electrophoretic profiles of normal and cancerous breast tissue. As discussed above, marker proteins useful in the invention are found primarily in the nuclear matrix of breast cancer tissue samples.

Nuclear matrix proteins were isolated from breast cancer tissue using a modification of the method of Fey, et al., *Proc. Natl. Acad. Sci.* (USA), 85: 121–125 (1988), incorporated by reference herein. Fresh breast cancer tissue specimens, ranging in size from about 0.2 g to about 1.0 g, were obtained from ten infiltrating ductal carcinomas from different patients. Samples were minced into small (1 mm$^3$) pieces and homogenized with a Teflon pestle on ice.

Nuclear matrix proteins from normal breast tissue were extracted as 50 mg to 100 mg samples from reduction mammoplasty patients. Samples were minced into small (1 mm$^3$) pieces and disaggregated overnight at 37° C. (5% $CO_2$) in a buffered salt solution (Hanks Balanced Salt Solution without $Ca^{++}/Mg^{++}$) containing antibiotics, 10% fetal calf serum, 1 mg/mL collagenase A (Boehringer Mannheim), and 0.5 mg/mL dispase (Boehringer Mannheim). Following disaggregation, cells were collected by centrifugation. Large aggregates were removed by filtration through nylon mesh (Nitex, 250 µM). Contaminating red blood cells were lysed in a solution of buffered ammonium chloride (0.31 M). The resulting cell suspension containing normal breast epithelial cells was washed and counted.

Both breast tumor and normal tissue, each prepared as described above, were treated with a buffered solution containing 0.5% Triton X-100, vanadyl ribonucleoside complex (RNase inhibitor, 5'–3') plus a protease inhibitor cocktail (phenylmethyl sulfonyl fluoride, Sigma, St. Louis, Mo.; and aprotinin and leupeptin, Boehringer Mannheim) to remove lipids and soluble protein.

Soluble cytoskeletal proteins were then removed by incubating the resulting pellet in an extraction buffer containing 250 mM $(NH_4)_2SO_4$, 0.5% Triton X-100, vanadyl ribonucleoside complex plus a protease inhibitor cocktail for 10 minutes on ice followed by centrifugation. Chromatin was removed by incubating the pellet in DNase I (100 micrograms per mL) in a buffered solution containing protease inhibitor cocktail for 45 minutes at 25° C.

The remaining pellet fraction, containing nuclear matrix protein, was solubilized in a disassembly buffer containing 8 M urea and protease inhibitor cocktail plus 1% 2-mercaptoethanol. Insoluble contaminants, primarily consisting of carbohydrates and extracellular matrix, were removed by ultracentrifugation. Target nuclear matrix proteins remained in the supernatant. Protein concentration was determined using a Coomassie Plus Protein Assay Kit (Pierce Chemicals, Rockford, Ill.) using a bovine gamma globulin standard. Proteins were then precipitated and stored at −80° C.

These proteins were next characterized by high-resolution 2-D gel electrophoresis using isoelectric focusing according to the procedure of O'Farrell, *J. Biol. Chem.*, 250: 4007–4021 (1975), on the Investigator 2-D system (Millipore, Bedford, Mass.). Nuclear matrix proteins were solubilized for isoelectric focusing analysis in a sample buffer containing 9 M urea, 65 mM 3-[(cholamidopropyl) dimethylamino]-1-propanesulfate (CHAPS), 2.2% ampholytes, and 140 mM dithiothreitol (DTT). One-dimensional isoelectric focusing was carried out for 18,000 volt-hours using 1 mm×18 mm gel tubes. Following first dimension electrophoresis, gels were extruded from gel tubes, equilibrated for 2 minutes in a buffer containing 0.3 M Tris base, 0.075 M Tris-HCl, 3.0% SDS, 50 mM DTT, and 0.0% bromophenol blue and placed on top of 1 mm 10% Tris-glycine-SDS Duracryl (Millipore) high tensile strength polyacrylamide electrophoresis slab gels. Second dimension slab gels were electrophoresed at 16 Watts per gel and 12° C. constant temperature for approximately 5 hours. Molecular weight standards consisted of bovine albumin ($M_r$ 66,000), ovalbumin ($M_r$ 45,000), glyceraldehyde-3-phosphate dehydrogenase ($M_r$ 36,000), carbonic anhydrase ($M_r$ 29,000), bovine pancreatic trypsinogen ($M_r$ 24,000), and soybean trypsin inhibitor ($M_r$ 20,100). Following electrophoresis, gels were fixed in a solution containing 40% ethanol/10% acetic acid followed by treatment with a solution containing 0.5% glutaraldehyde. Gels were washed extensively and silver stained according to the method of Rabillioud, et al., *Electrophoresis*, 13: 429–439 (1992) and dried between sheets of cellophane paper.

Silver-stained gels were imaged using a MasterScan Biological Imaging System (CSP, Inc., Billerica, Mass.) according to the manufacturer's instructions. Digital filtering algorithms were used to remove both uniform and non-uniform background without removing critical image data. Two-D scan (TM) two-dimensional gel analysis and database software (version 3.1) using multiple Gaussian least-squares fitting algorithms were used to compute spot patterns into optimal-fit models of the data as reported by Olson, et al., *Anal. Biochem.*, 169: 49–70 (1980). Triangulation from the internal standards was used to precisely determine the molecular weight and isoelectric point of each target protein of interest. Interpretive densitometry was performed using specific software application modules to integrate the data into numeric and graphical reports for each gel being analyzed.

Figure 2:
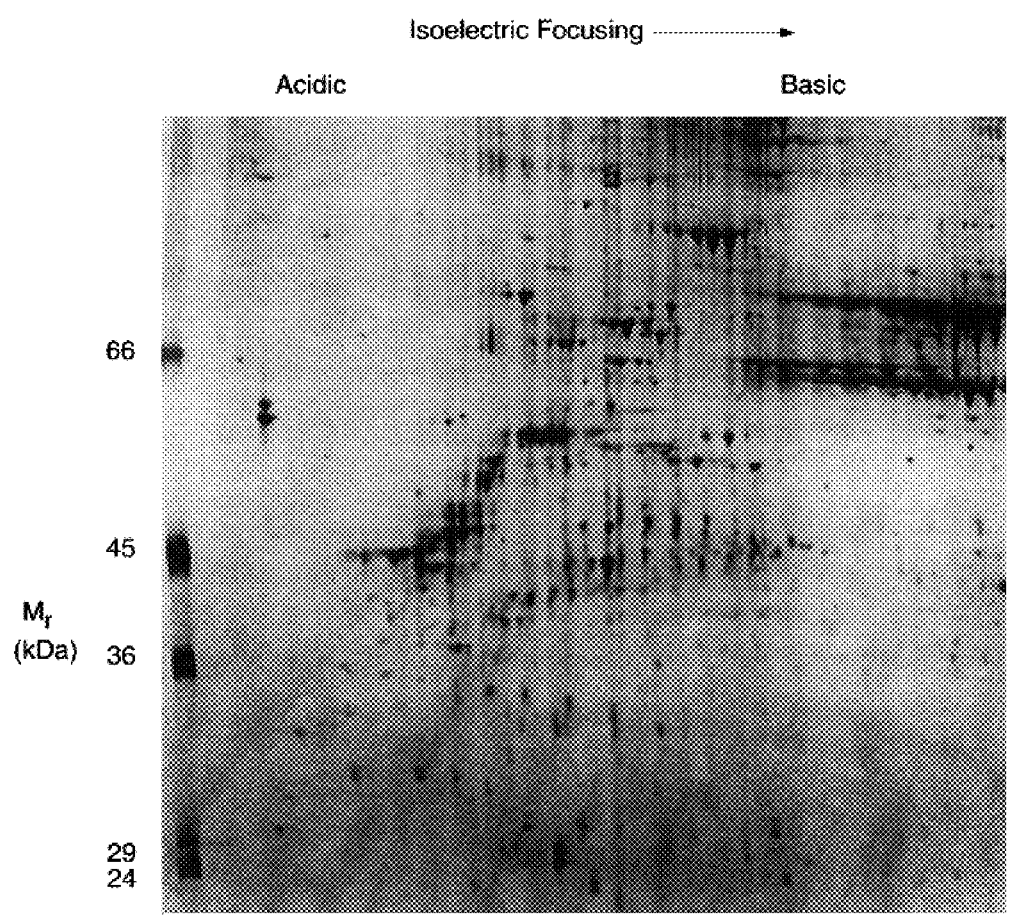
FIG. 2 is a two-dimensional gel electrophoresis pattern produced by nuclear matrix proteins obtained from a normal breast tissue sample.

The results of 2-D gel electrophoresis analysis are shown in FIGS. 1 and 2. FIG. 1 shows a typical gel pattern produced by nuclear matrix proteins obtained from a normal breast tissue sample. FIG. 2 shows a typical breast cancer-associated nuclear matrix protein pattern obtained from breast cancer tissue. Comparison of FIGS. 1 and 2 reveals that, while most proteins in the cancer and non-cancer samples are identical, there are eight proteins that are unique to the breast cancer sample (labeled in FIG. 1). Table 1 identifies those proteins, designated BC-1 through BC-8, by their approximate molecular weight and isoelectric point. Both the molecular weight and isoelectric point values listed in Table 1 are approximate and accurate to within 1,000 Daltons for molecular weight and to within 0.2 pH units for isoelectric point.

TABLE 1

| Peptide | Molecular Weight | Observed Isoelectric Point | Actual Isoelectric Point | Breast Cancer | Normal Breast |
|---|---|---|---|---|---|
| BC-1 | 80,735 | 5.24 |  | + | − |
| BC-2 | 32,490 | 6.82 | 5.69 | + | − |
| BC-3 | 28,969 | 5.66 |  | + | − |
| BC-4 | 28,723 | 6.83 |  | + | − |
| BC-5 | 31,111 | 5.36 |  | + | − |
| BC-6 | 22,500 | 5.58 | 4.64 | + | − |
| BC-7 | 38,700 | 6.90 |  | + | − |
| BC-8 | 33,000 | 6.44 | 5.26 | + | − |

Three of the breast cancer-associated nuclear matrix proteins that are specific to breast cancer cells were isolated and processed for tryptic peptide mapping and amino acid sequencing.

Three of the breast cancer-associated nuclear matrix proteins were partially sequenced. The nuclear matrix fraction from a single human breast adenocarcinoma was electrophoresed on 10% two-dimensional gels in the manner described above. Thereafter, proteins were visualized by soaking the gels in 200 mM imidazole for 10 minutes and then rinsing for 1 minute in water, followed by 1–2 minutes in 300 mM zinc chloride. After protein-containing spots began to appear, the gels were placed in water and relevant gel spots were excised. The isolated gel spots, each representing individual breast cancer-associated nuclear matrix proteins, were pooled. Destaining was accomplished by washing for 5 minutes in 2% citric acid followed by several washes in 100 mM Tris hydrochloride at pH 7.0 in order to raise the pH within the isolated gel spots.

Each set of pooled gel spots was then diluted with an equal volume of 2×SDS-PAGE sample buffer (250 mM Tris-Cl, 2% SDS, 20% glycerol, 0.01% bromophenol blue, 10% β-mercaptoethanol, pH 6.8) and incubated at 75° C. for 3 minutes. Samples were then cooled on ice and loaded into the lanes of a 4% polyacrylamide stacking/11% polyacrylamide separating SDS-PAGE gel. Electrophoresis was accomplished in 1× Tank buffer (25 mM Tris-HCl, 192 mM glycine, 1% SDS, pH 8.3) to focus gel spots into bands. Molecular weight markers (BioRad #161-0304) were used on each gel to compare the observed molecular weights on one- and two-dimensional gels.

The gels were then electroblotted onto Immobilon-PVDF membranes (Millipore) according to the method reported in Towbin, et al., *Proc. Nat'l. Acad. Sci.*, 76: 4350–4354 (1979), as modified for a mini-gel format by Matsudaira, et al., *J. Biol. Chem.*, 262: 10035 (1987), incorporated by reference herein. Membranes were then stained for 1 minute with 0.1% Buffalo Black (1% acetic acid, 40% methanol) and rinsed with water. Regions containing polypeptide bands were then excised with a scalpel.

The resulting PVDF-bound polypeptides were then subjected to tryptic peptide mapping and microsequencing by the method of Fernandez, et al., *Analytical Biochem.*, 218: 112–117 (1994), incorporated by reference herein, using a Hewlett-Packard Model 1090M HPLC. Sequence determinations were made on an Applied Biosystems ProCise Sequenator. Most sequences were confirmed by MALDI-TOF mass spectrometry of the individual peptides.

The results of sequencing of the BC-2, BC-6, and BC-8 peptide fragments are provided in Table 2 below.

TABLE 2

| Peptide | Fragments Sequenced | SEQ ID NO. | Predicted Mass | Observed Mass |
|---|---|---|---|---|
| BC-6 | DLISHDEMFSDIYK | 1 | 1714.55 | 1712.9 |
|  | TEGNIDDSLIGGNASA | 2 | 4859.22 | 4859.19 |
| BC-2 | KAEAAASAL | 3 | — | — |
|  | KFVLMR | 4 | — | — |
|  | ANIQAVSLK | 5 | — | — |
| BC-8 | SDVVPMTAENFR | 6 | 1367.21 | 1365.5 |
|  | IIPQFMCQGGDFXNHR | 7 | 2296.44 | 2293.3 |
|  | KFDDENFILR | 8 | 1269.97 | 1268.4 |
|  | HVVFGEVTEGLDVLR | 9 | 1670.93 | 1669.9 |
|  | VIIADCGEY | 10 |  |  |

As shown in Table 2, two fragments of the peptide designated BC-6 were sequenced. Analysis in the GenBank database revealed that those sequence fragments (SEQ ID NOS: 1 and 2) are identical to portions of the translationally-controlled tumor protein (TCTP). The TCTP protein is abundantly transcribed under strict translational control in mouse and human tumor cell lines. However, its function is unknown.

A large, contiguous sequence, designated BC-2 (SEQ ID NO: 12), was obtained based upon the three smaller fragments shown in Table 2 (SEQ ID NOS: 3–5). A search in the GenBank database revealed an expressed sequence tag cDNA clone encoding an amino acid sequence substantially identical to that of the BC-2 fragment. The coding sequence is shown in SEQ ID NO: 11. While the expressed sequence tag corresponding to a portion of the BC-2 fragment does not clearly fit into any known molecular family, there is an homology between a segment of BC-2 and a putative 16.7 Kda protein encoded by a gene on yeast chromosome XI. The function of the yeast protein is not known.

Finally, an approximately 33,000 Dalton breast cancer-associated nuclear matrix protein having an isoelectric point of approximately 6.44 was sequenced from the 2D gels described above. That protein, designated BC-8, was partially sequenced to produce five sequence fragments, shown in SEQ ID NOS: 6–10, respectively. A search in the GenBank database revealed a high degree of homology between each of those five sequences and portions of the amino acid sequences of several members of the cyclophilin superfamily. The BC-8 peptide appears to contain a typical cyclophilin domain of about 150 amino acids that is about 70% identical to cyclophilin A, the archetypal member of the cyclophilin superfamily.

In addition, the data indicate that there are at least two distinct RNA isoforms encoding BC-8. The observed amino acid sequences corresponding to each isoform are shown in SEQ ID NOS: 18 and 20.

Breast cancer-associated nuclear matrix proteins may be identified based upon the partial amino acid and nucleotide sequences provided above using well-known techniques. Thus, breast cancer-associated nuclear matrix proteins detected according to methods of the invention may be referred to as comprising a continuous sequence shown in the above-noted sequence fragments. The skilled artisan understands, for example, that fragments provided above are sufficient to provide an epitope for binding of an antibody directed against a breast cancer-associated nuclear matrix protein. Moreover, nucleotide sequences encoding the fragments described above are sufficient for hybridization using complementary oligonucleotide probes.

B. Isolation of Breast Cancer Marker Proteins by Recombinant Methods.

The BC-2 and BC-8 marker proteins of the invention were also isolated by recombinant methods in order to obtain the full-length sequence of each.

The 5' ends of cDNA encoding the BC-8 protein (isoform A) were obtained using a 5'-RACE (rapid amplification of cDNA ends) kit according to the Manufacturer's instructions (Life Technologies, Bethesda, Md.) using breast cancer cDNA obtained from Invitrogen. The antisense primer, 5'-ACTTCTTCCCATAGATGGACTTG-3' (SEQ ID NO: 21), was used to amplify full-length cDNA encoding isoform A of the BC-8 protein.

Figure 7:
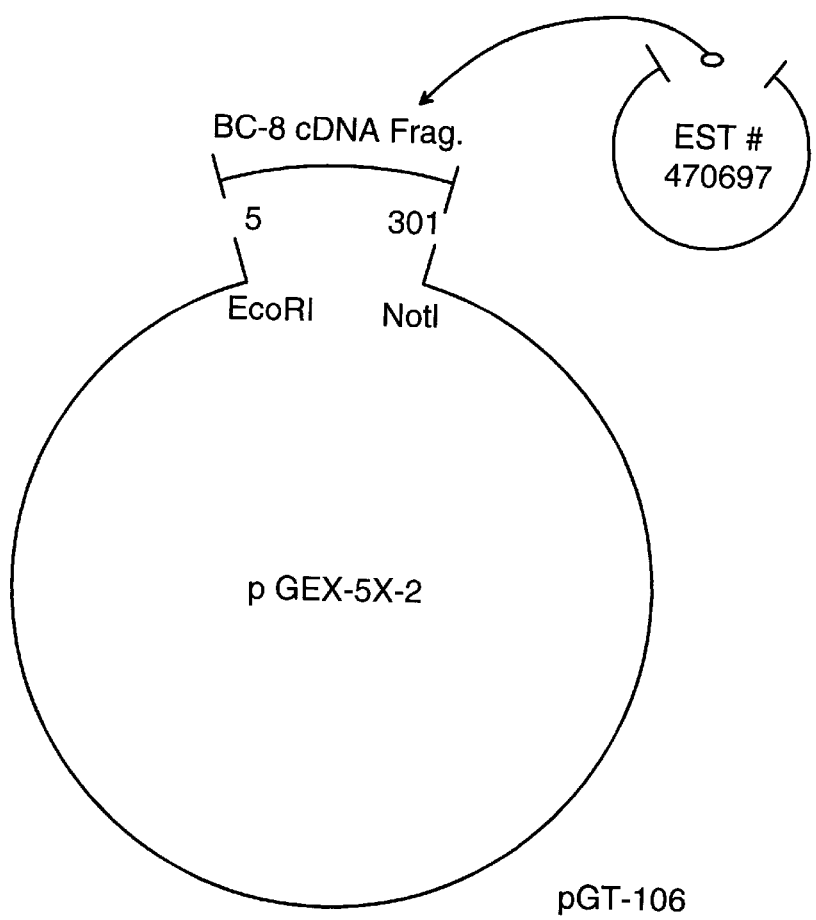
FIG. 7 is a schematic diagram of plasmid pGT106.

This cDNA was placed into one of two recombinant expression vector in order to express the protein. A first vector contained a glutathione-S-transferase fusion gene comprising the BC-8 cDNA. That vector was constructed by inserting an EcoRI/NotI fragment (bases 71-1307 of SEQ ID NO: 17) from EST clone #470697 into plasmid pGEX-5X-2 (Pharmacia, Piscataway, N.J.). The fragment comprised Codons 5 through 301 of the BC-8 sequence. The plasmid was renamed pGT106, and is shown in FIG. 7. The BC-8 protein was expressed from pGT106 by standard methods.

Figure 8:
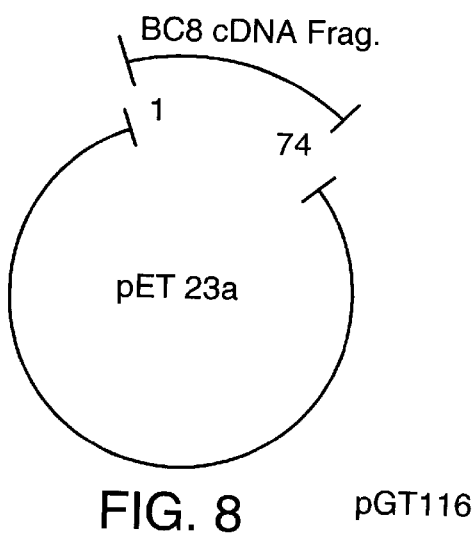
FIG. 8 is a schematic diagram of plasmid pGT116.

A second vector contained DNA encoding a T7-gene10 (his)$_6$ BC-8A$_{1-74}$ fusion protein. A DNA fragment encoding amino acids 1–74 of BC-8A was obtained by amplification from plasmid pGT106. The primers were: 5'-CGCGCGGATCCATGGCCACCACCAAGCGC-3' (SEQ ID NO: 22) and 5'-CTGCTCGAGTGCGGCCGCTCCAAAAAGCTCAG ATTC-3' (SEQ ID NO: 23). The amplified fragment was cloned into a BamHI/NotI site in plasmid pET23a (Novagen, San Diego, Calif.) to form plasmid pGT116. That plasmid is shown in FIG. 8. The fusion protein was expressed, and purified on a 2 ml AminoLink Plus Column (Pierce, Rockford, Ill.) according to the Manufacture's instructions. The resulting full-length BC-8A amino acid sequence is shown in SEQ ID NO: 16. Sequencing of the EST clones ##85389, 267725 and of PBLU2-2a (nucleotides 76–878 of EST clone # 85389) provided the full-length BC-2 amino acid sequence shown in SEQ ID NO: 15.

EXAMPLE 2

Production of Antibodies Against Marker Proteins

Once identified, a breast cancer-associated protein, such as a nuclear matrix protein, may be detected using gel electrophoresis techniques available in the art, as disclosed, for example, in Maniatis et al., "Molecular Cloning: A Laboratory Manual," Cold Spring Harbor Press, (1989). In 2-D gel electrophoresis, proteins are first separated in a pH gradient gel according to their isoelectric point. This gel is then placed on a polyacrylamide gel and the proteins are separated according to molecular weight. (See, e.g., O'Farrell, *J. Biol. Chem.* 250: 4007–4021 (1975) and Example 1, supra).

Through this method, one or more proteins associated with breast cancer may be detected by isolating proteins from a sample, such as a breast tissue cell sample from a patient, and then separating the proteins by two dimensional gel electrophoresis to produce a characteristic two dimensional gel electrophoresis pattern. The pattern then may be compared with a standard gel pattern derived from normal or cancer cells processed under identical conditions. The standard may be stored or obtained in an electronic database of electrophoresis patterns. The presence of a breast cancer-associated protein in the two-dimensional gel provides an indication of the presence of breast cancer in the sample being tested. The detection of two or more breast cancer-associated proteins increases the stringency of methods according to the invention.

A breast cancer-associated protein, such as a nuclear matrix protein, may also be detected in a tissue or body fluid sample using numerous binding assays that are well known to those of ordinary skill in the art. For example, a target protein in a sample may be reacted with a binding moiety capable of specifically binding the target protein. The binding moiety may comprise, for example, a member of a ligand-receptor pair (i.e., a pair of molecules capable of specific binding interactions), antibody-antigen, enzyme-substrate, nucleic acid-nucleic acid, protein-nucleic acid, or other specific binding pairs known in the art. Binding proteins may be designed which have enhanced affinity for a target protein. Optionally, the binding moiety may be linked to a detectable label, such as an enzymatic, fluorescent, radioactive, phosphorescent or colored particle label. The labeled complex may be detected visually or with a spectrophotometer or other detector.

Suitable kits for detecting breast cancer-associated proteins include a receptacle or other means for capturing a sample to be evaluated, and means for detecting the presence and/or quantity in the sample of one or more of the breast cancer-associated proteins described herein. Where the presence of a protein within a cell is to be detected, the kit also may comprise means for disrupting the cell structure so as to expose intracellular proteins.

A breast cancer-associated protein or normal breast cell-associated protein in a sample also may be detected using immunoassay techniques available in the art. The isolated breast cancer-associated proteins or normal breast cell-associated proteins also may be used for the development of diagnostic and other tissue-evaluating kits and assays.

Antibodies to isolated target breast cancer-associated or normal breast tissue-associated proteins that are useful in assays for detecting breast cancer in an individual may be generated using standard immunological procedures well known and described in the art. See, for example, *Practical Immunology*, Butt, N. R., ed., Marcel Dekker, N.Y., 1984. Briefly, an isolated target protein is used to raise antibodies in a xenogeneic host, such as a mouse, goat or other suitable mammal. Preferred antibodies are antibodies that bind specifically to an epitope on the protein, preferably having a binding affinity greater than $10^5$ M$^{-1}$, most preferably having an affinity greater than $10^7$ M$^{-1}$ for that epitope.

The protein is combined with a suitable adjuvant capable of enhancing antibody production in the host, and injected into the host, for example, by intraperitoneal administration. Any adjuvant suitable for stimulating the host's immune response may be used to advantage. A commonly used adjuvant is Freund's complete adjuvant (an emulsion comprising killed and dried microbial cells, e.g., from Calbiochem Corp., San Diego, or Gibco, Grand Island, N.Y.). Where multiple antigen injections are desired, the subsequent injections comprise the antigen in combination with an incomplete adjuvant (e.g., cell-free emulsion).

Antibodies against the T7-gene 10/(His)$_6$/BC-8A$_{1-74}$ protein and a BC-2 partial sequence synthetic peptide LADADADLEERLKNLRRD (SEQ ID NO: 24) conjugated to rabbit serum albumin, were made in rabbits at Quality Controlled Biochemicals (Hopkinton, Mass.).

Polyclonal antibodies were isolated from the antibody-producing hosts by extracting serum containing antibodies to the protein of interest. For example, antibodies against BC-8 were purified by adsorption of whole antiserum onto T7-gene 10/(His)$_6$/BC-8A$_{1-74}$-affinity resin. The specific antibody was eluted by pH shock at pH 3.0, then buffer-exchanged into PBS (pH 7.4) using a Centricon-3 filtration unit (Amicon, Beverly, Mass.). Likewise, the antibodies against BC-2 were purified by adsorption of whole antiserum onto peptide-affinity resin and isolated in the same manner.

Monoclonal antibodies may also be produced by isolating host cells that produce the desired antibody, fusing these cells with myeloma cells using standard procedures known in the immunology art, and screening for hybrid cells (hybridomas) that react specifically with the target protein and have the desired binding affinity.

Provided below is an exemplary protocol for monoclonal antibody production, which is currently preferred. Other protocols also are envisioned. Accordingly, the particular method of producing antibodies to target proteins is not envisioned to be an aspect of the invention.

Monoclonal antibodies to any target protein, and especially a nuclear matrix protein associated with breast cancer may be readily prepared using methods available in the art, including those described in Kohler, et al., *Nature*, 256: 495 (1975) for fusion of myeloma cells with spleen cells.

EXAMPLE 3

Detection of Breast Cancer-Associated Proteins

Breast cancer marker proteins, such as BC-2 and BC-8, may be detected by numerous methods (e.g., RIA, sandwich immunoassays, and Western blots). For purposes of exemplification, BC-2 and BC-8 proteins were detected in breast tumor samples by Western blotting. Protein samples (Collaborative Human Tissue Network) were electrophoresed on a 4–20% SDS-PAGE gradient gel (Novex, San Diego, Calif.), and then transferred to BA-S-85 supported nitrocellulose membrane (Schleicher & Schuell, Keene, N.H.) using standard protocols. The gel was incubated with anti-BC-8 antibodies, as described above, for 60 minutes at room temperature. Unbound antibody was washed away, and bound antibody was detected using horseradish peroxidase conjugated secondary antibody (Jackson Immunoresearch, West Grove, Pa.) and the Enhanced Chemiluminescense reagent system (Amersham, Arlington Heights, Ill.) according to the Manufacture's instructions. Detection for BC-2 proteins was conducted in the same manner.

Figure 3:
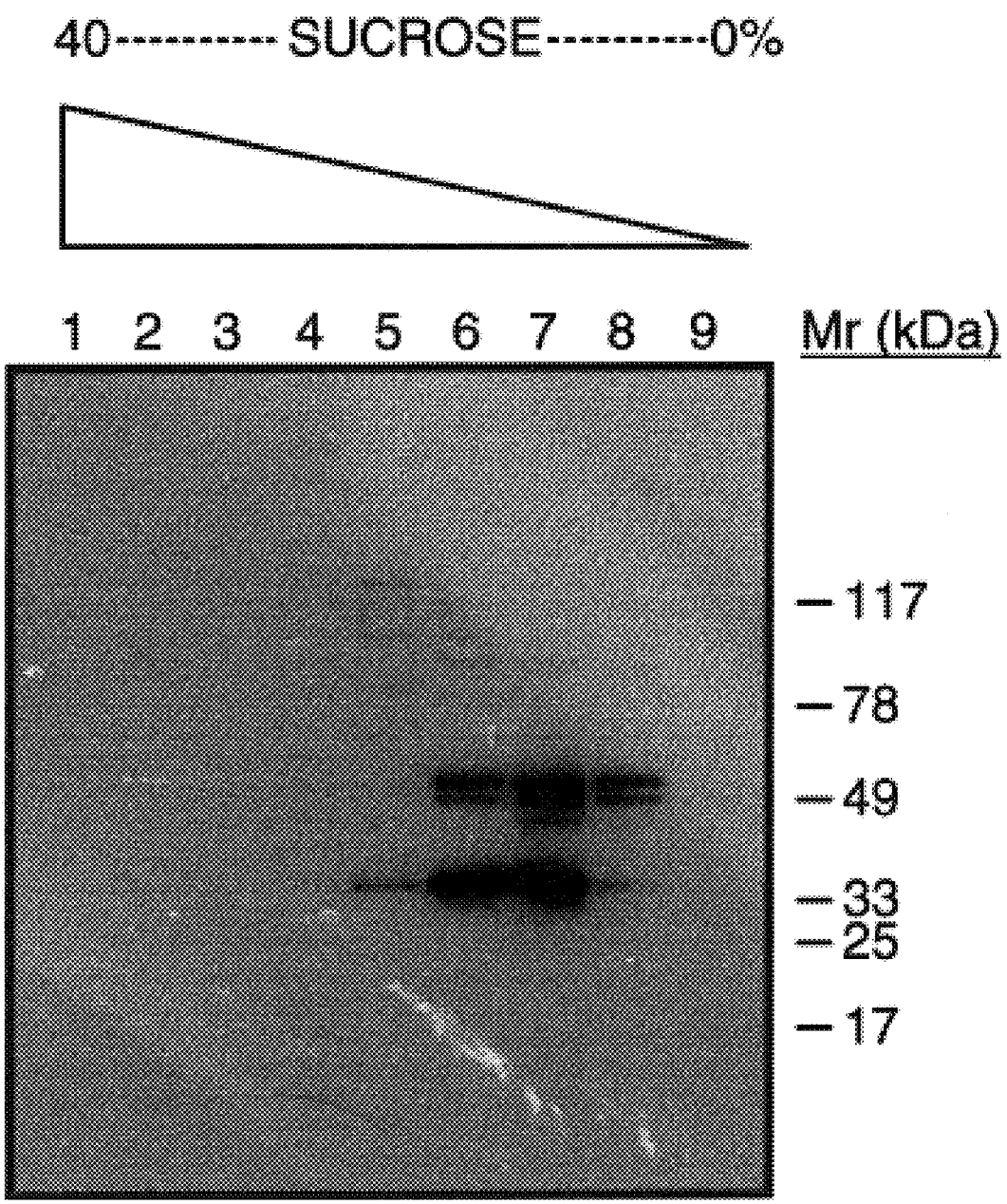
FIG. 3 is a western blot of fractions collected from a 10–40% sucrose density gradient of fractionated MCF-7 cell nuclei probed with BC-8 specific antibody. The doublet at about 35,000 Daltons represents the two isoforms of BC-8, BC-8A (SEQ ID NO: 18) and BC-8B (SEQ ID NO: 20).

In one Western blot, fractions from a 10–40% sucrose density gradient of MCF-7 cell nuclei were run on a 4–20% SDS PAGE gel. Once the proteins had been blotted onto a nitrocellulose membrane, the membrane was probed with anti-BC-8 antibodies. These antibodies were able to detect the presence of BC-8 proteins in the sample as shown in FIG. 3. The doublet at about 35,000 Daltons represents the two isoforms of BC-8, BC-8A (SEQ ID NO: 18) and BC-8B (SEQ ID NO: 20).

Figure 5:
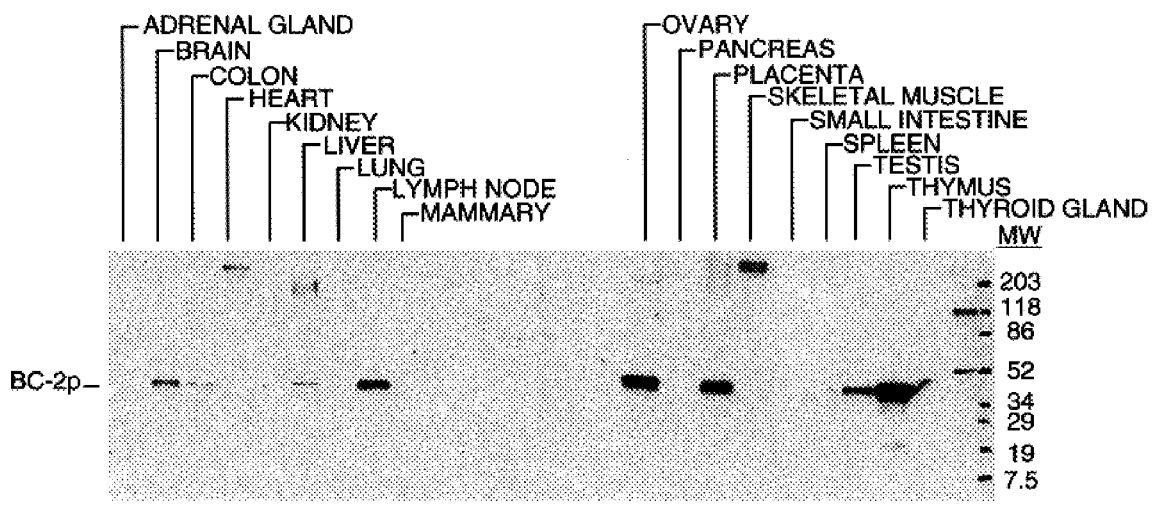
FIG. 5 is a western blot, each lane containing 10 ug of total protein from the source indicated. The blot was probed with BC-2p specific antibody. The doublet at about 35,000 Daltons represents the two major apparent isoforms of BC-2.

In another Western blot, 10 μgs of various normal human tissues were run on a gel and transferred to membrane in a manner similar to that used above. For this blot anti-BC-2 antibodies was used as the probe. The results are shown in FIG. 5. Although there was detection of BC-2 protein in other tissues, BC-2 proteins were not detected in normal mammary tissue.

Figure 6A:
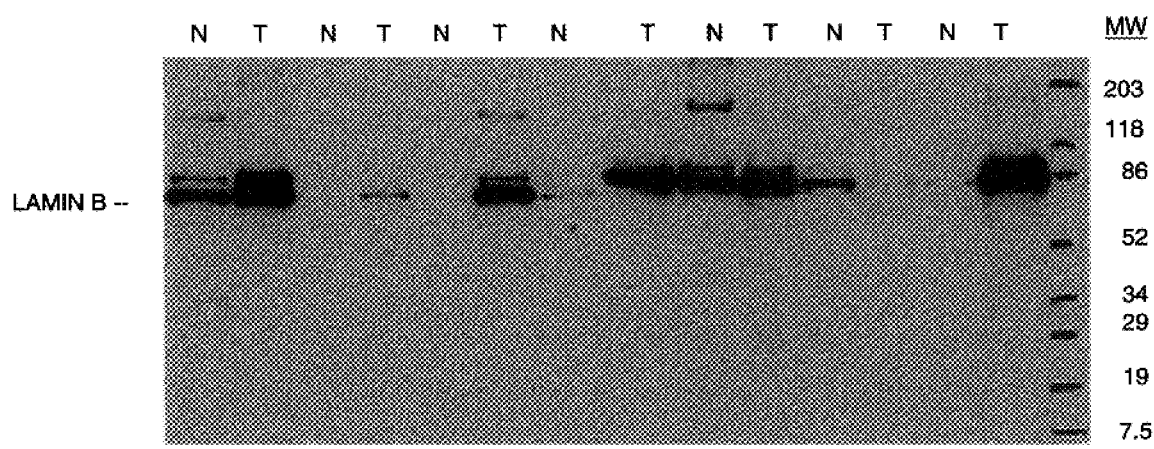
FIG. 6 is a panel of two western blots. Each lane contains 10 ug of total protein from normal (N) or tumor (T) tissue source, as indicated. The upper blot was probed with Lamin B specific antibody. The lower blot was probed with BC-2p specific antibody. The doublet at about 35,000 Daltons represents the two major isoforms of BC-2p.
Figure 6B:
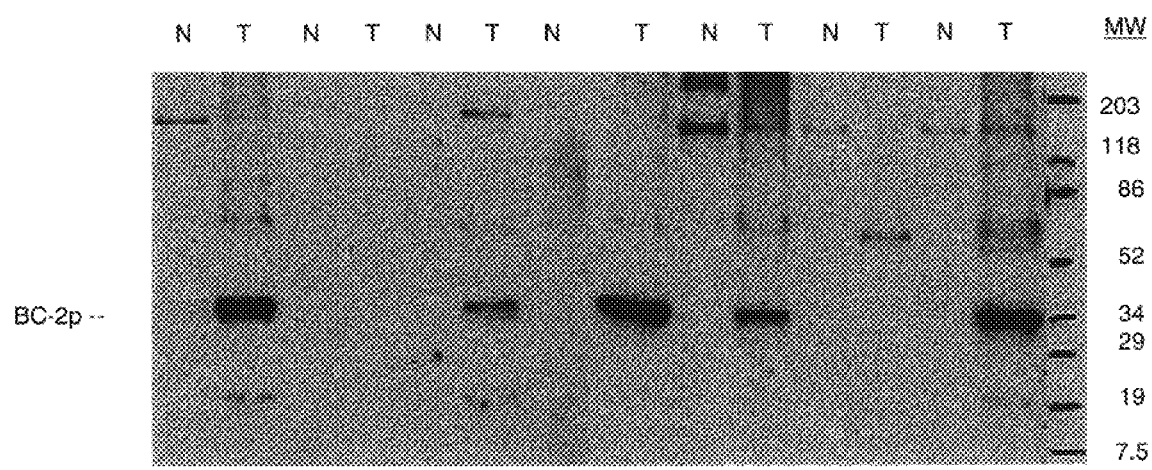

In a further experiment, 10 ug total protein from normal (N) and tumor (T) breast tissue, in alternate lanes, were run on a gel and blotted, as described above. One set of tissue samples was probed with Lamin B and the other with anti-BC-2p antibodies. The BC-2 protein was detected in most of the tumor tissue samples, but BC-2 proteins were undetectable in normal tissue samples as shown in FIG. 6.

EXAMPLE 4

Use of Nucleic Acids to Detect Breast Cancer

The presence of breast cancer also may be determined by detecting, in a tissue or body fluid sample, a nucleic acid molecule encoding a breast cancer-associated protein. A nucleic acid encoding BC-2 is shown in SEQ ID NO: 15, a nucleic acid encoding BC-8A is shown in SEQ ID NO: 17, and a nucleic acid encoding BC-8B is shown in SEQ ID NO: 19.

A target nucleic acid molecule, encoding a breast cancer-associated protein, may be detected using a binding moiety, optionally labeled, capable of specifically binding the target nucleic acid. The binding moiety may comprise, for example, a protein or a nucleic acid. Additionally, a target nucleic acid, such as an mRNA encoding a breast cancer-associated nuclear matrix protein, may be detected by conducting a northern blot analysis using labeled oligonucleotides, (e.g., a nucleic acid fragment complementary to and capable of hybridizing specifically with at least a portion of a target nucleic acid). While any length oligonucleotide may be utilized to hybridize an mRNA transcript, oligonucleotides typically within the range of 8–100 nucleotides, preferably within the range of 15–50 nucleotides, are envisioned to be most useful in standard RNA hybridization assays.

The oligonucleotide selected for hybridizing to the target nucleic acid, whether synthesized chemically or by recombinant DNA techniques, is isolated and purified using standard techniques and then preferably labeled (e.g., with $^{35}$S or $^{32}$P) using standard labeling protocols. A sample containing the target nucleic acid then is run on an electrophoresis gel, the dispersed nucleic acids transferred to a nitrocellulose filter and the labeled oligonucleotide exposed to the filter under suitable hybridizing conditions, e.g. 50% formamide, 5×SSPE, 2×Denhardt's solution, 0.1% SDS at 42° C., as described in Maniatis et al., "Molecular Cloning: A Laboratory Manual," Cold Spring Harbor Press, (1989). Other useful procedures known in the art include solution hybridization, and dot and slot RNA hybridization. The amount of the target nucleic acid present in a sample then optionally is quantitated by measuring the radioactivity of hybridized fragments, using standard procedures known in the art.

Using these procedures, mRNA encoding BC-8 was detected on commercially available Northern blots (Invitrogen, San Diego, Calif.). A $^{32}$P-labelled NotI/EcoRI fragment of the BC-8 cDNA clone, used above in the construction of plasmid pGT106, was used to probe several Northern blots. Each blot contained alternating lanes of 20 ug of total RNA of normal (N) and tumor (T) tissue for a specific type of tissue; rectum, lung, breast, and colon. A final blot contained normal tissue samples from various tissues, heart, brain, kidney, liver, lung, pancreas, spine, skeletal muscle. The two bands at 1.6 and 1.8 kb represent the two mRNAs of BC-8, BC-8A (SEQ ID NO: 17) and BC-8B (SEQ ID NO: 19) as shown in FIG. 4.

Following a similar protocol, oligonucleotides also may be used to identify other sequences encoding members of the target protein families. The methodology also may be used to identify genetic sequences associated with the nucleic acid sequences encoding the proteins described herein, e.g., to identify non-coding sequences lying upstream or downstream of the protein coding sequence, and which may play a functional role in expression of these genes. Additionally, binding assays may be conducted to identify and detect proteins capable of a specific binding interaction with a nucleic acid encoding a breast cancer-associated protein, which may be involved e.g., in gene regulation or gene expression of the protein. In a further embodiment, the assays described herein may be used to identify and detect nucleic acid molecules comprising a sequence capable of recognizing and being specifically bound by a breast cancer-associated nuclear matrix protein.

EXAMPLE 5

Identification and Therapeutic Use of Compounds that Interact With Breast Cancer-Associated Proteins Methods are provided to screen small molecules for those that inhibit the function of breast cancer-associated proteins. Such methods typically involve construction of a screening system in which breast cancer-associated proteins are linked to DNA binding proteins that are responsible, in part, for transcription initiation.

cDNA encoding peptides or peptide fragments capable of interacting with breast cancer-associated proteins (BCAPs) are determined using a two-hybrid assay as reported in Durfee, et al., *Genes & Develop.*, 7: 555–559 (1993), incorporated by reference herein. The two-hybrid assay is based upon detection of the expression of a reporter gene which is only produced when two fusion proteins, one comprising a DNA-binding domain and one comprising a transcription initiation domain, interact.

A host cell that contains one or more reporter genes, such as yeast strain Y153, reported in Durfee, Supra., is used. Expression of the reporter genes is regulated by the Gal4 promoter. However, the host cell is deleted for Gal4 and its negative regulator, Gal80. Thus, host cells are turned off for expression of the reporter gene or genes which are coupled to the uasg (the Gal upstream activating sequence).

Two sets of plasmids are then made. One contains DNA encoding a Gal4 DNA-binding domain fused in frame to DNA encoding a breast cancer-associated protein (BCAP). A second list of plasmids contains DNA encoding a Gal4 activation domain fused to portions of a human cDNA library constructed from human lymphocytes. Expression from the first plasmid results in a fusion protein comprising a Gal4 DNA-binding domain and a BCAP. Expression from the second plasmid produces a transcription activation protein fused to an expression product from the lymphocyte cDNA library. When the two plasmids are transformed into a gal-deficient host cell, such as the yeast Y153 cells described above, interaction of the Gal DNA binding domain and transcription activation domain will occur only if the BCAP that is fused to the DNA binding domain binds to a protein expressed from the lymphocyte cDNA library fused to the transcription activating domain. The result of such a fusion is transcription initiation and expression of the reporter gene. A schematic diagram showing the aforementioned relationship is found in FIG. 3.

EXAMPLE 6

Identification of Inhibitory Compounds

The invention also provides means for identifying compounds, including small molecules, which inhibit specific interaction between a breast cancer-associated protein and its binding partner. In these methods, a host cell is transfected with DNA encoding a suitable DNA binding domain/breast cancer-associated protein hybrid and a translation activation domain/putative breast cancer-associated protein binding partner as disclosed above.

The host cell also contains a suitable reporter gene in operative association with a cis-acting transcription activating element recognized by the transcription factor DNA binding domain. One particularly useful reporter gene is the luciferase gene. Others include the lacZ gene, HIS3, LEU2, and GFP (Green Fluorescent Protein) genes. The level of reporter gene expressed in the system is first assayed. The host cell is then exposed to the candidate molecule and the level of reporter gene expression is detected. A reduction in reporter gene expression is indicative of the candidate's ability to interfere with complex formation or stability with respect to the breast cancer-associated protein. As a control, the candidate molecule's ability to interfere with other, unrelated protein-protein complexes is also tested. Molecules capable of specifically interfering with a breast cancer-associated protein/binding partner interaction, but not other protein-protein interactions, are identified as candidates for production and further analysis. Once a potential candidate has been identified, its efficacy in modulating cell cycling and cell replication can be assayed in a standard cell cycle model system.

Candidate molecules can be produced as described herein. In addition, derivatives of candidate sequences can be created having, for example, enhanced binding affinity.

EXAMPLE 7

Production of BCAP Binding Proteins

DNA encoding breast cancer-associated proteins can be inserted, using conventional techniques well described in the art (see, for example, Maniatis (1989) Molecular Cloning A Laboratory Manual), into any of a variety of expression vectors and transfected into an appropriate host cell to produce recombinant proteins, including both full length and truncated forms. Useful host cells include *E. coli, Saccharomyces cerevisiae, Pichia pastoris*, the insect/baculovirus cell system, myeloma cells, and various other mammalian cells. The full length forms of the proteins of this invention are preferably expressed in mammalian cells, as disclosed herein. The nucleotide sequences also preferably include a sequence for targeting the translated sequence to the nucleus, using, for example, a sequence encoding the eight amino acid nucleus targeting sequence of the large T antigen, which is well characterized in the art. The vector can additionally include various sequences to promote correct expression of the recombinant protein, including transcription promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest can also be manipulated to remove potentially inhibiting sequences or to minimize unwanted secondary structure formation. As will be appreciated by the practitioner in the art, the recombinant protein can also be expressed as a fusion protein.

After translation, the protein can be purified from the cells themselves or recovered from the culture medium. The DNA can also include sequences which aid in expression and/or purification of the recombinant protein. The DNA can be expressed directly or can be expressed as part of a fusion protein having a readily cleavable fusion junction. An exemplary protocol for prokaryote expression is provided below. Recombinant protein is expressed in soluble form or in inclusion bodies, and can be purified therefrom using standard technology.

The DNA may also be expressed in a suitable mammalian host. Useful hosts include fibroblast 3T3 cells, (e.g., NIH 3T3, from CRL 1658) COS (simian kidney ATCC, CRL-1650) or CHO (Chinese hamster ovary) cells (e.g., CHO-DXB11, from Lawrence Chasin, *Proc. Nat'l. Acad. Sci.* (1980) 77(7):4216–4222), mink-lung epithelial cells (MV1Lu), human foreskin fibroblast cells, human glioblastoma cells, and teratocarcinoma cells. Other useful eukaryotic cell systems include yeast cells, the insect/baculovirus system or myeloma cells.

To express a breast cancer-associated binding protein, the DNA is subcloned into an insertion site of a suitable, commercially available vector along with suitable promoter/enhancer sequences and 3' termination sequences. Useful promoter/enhancer sequence combinations include the CMV promoter (human cytomegalovirus (MIE) promoter) present, for example, on pCDM8, as well as the mammary tumor virus promoter (MMTV) boosted by the Rous sarcoma virus LTR enhancer sequence (e.g., from Clontech, Inc., Palo Alto). A useful inducible promoter includes, for example, A $Zn^{2+}$ induceable promoter, such as the $Zn^{2+}$ metallothionein promoter (Wrana et al. (1992) *Cell* 71:1003–1014.) Other inducible promoters are well known in the art and can be used with similar success. Expression also can be further enhanced using transactivating enhancer sequences. The plasmid also preferably contains an amplifiable marker, such as DHFR under suitable promoter control, e.g., SV40 early promoter (ATCC #37148). Transfection, cell culturing, gene amplification and protein expression conditions are standard conditions, well known in the art, such as are described, for example in Ausubel et al., ed., *Current Protocols in Molecular Biology*, John Wiley & Sons, N.Y. (1989). Briefly, transfected cells are cultured in medium containing 5–10% dialyzed fetal calf serum (dFCS), and stably transfected high expression cell lines obtained by amplification and subcloning and evaluated by standard Western and Northern blot analysis. Southern blots also can be used to assess the state of integrated sequences and the extent of their copy number amplification.

The expressed protein is then purified using standard procedures. A currently preferred methodology uses an affinity column, such as a ligand affinity column or an antibody affinity column. The bound material is then washed, and receptor molecules are selectively eluted in a gradient of increasing ionic strength, changes in pH, or addition of mild detergent.

The therapeutic efficacy of treating breast cancer with inhibitors of breast cancer-associated proteins according to the invention is measured by the amount of breast cancer-associated nuclear matrix protein released from breast cancer cells that are undergoing cell death. As reported in PCT publication WO93/05432 (U.S. Pat. No. 92/9220, filed Oct. 29, 1992), incorporated by reference herein, soluble nuclear matrix proteins and fragments thereof are released by cells upon cell death. Such soluble nuclear matrix proteins can be quantitated in a body fluid and used to monitor the degree or rate of cell death in a tissue. For example, the concentration of body fluid-soluble nuclear matrix proteins or fragments thereof released from cells is compared to standards from healthy, untreated tissue. Fluid samples are collected at discrete intervals during treatment and compared to the standard. Changes in the level of soluble breast cancer-associated nuclear matrix protein are indicative of the efficacy of treatment (i.e., the rate of cancer cell death). Appropriate body fluids for testing include blood, serum, plasma, urine, semen, sputum, breast exudate.

Thus, breast cancer may be identified by the presence of breast cancer-associated nuclear matrix proteins as taught herein. Once identified in this way, breast cancer may be treated using inhibitors of the nuclear matrix proteins and the progress of such treatment, including dosing considerations, may be monitored by the release of soluble breast cancer-associated nuclear matrix proteins from breast cancer cells which have died or are dying as a result of such treatment. Similarly, monitoring the release of soluble nuclear matrix proteins from breast cancer cells is useful for monitoring the treatment of breast cancer by means other than those reported herein or such other means in combination with treatment means reported herein.

Those skilled in the art will know, or be able to ascertain using no more than routine experimentation, many equivalents to the specific embodiments of the invention described herein. These and all other equivalents are intended to be encompassed by the following claims.

What is claimed is:

1. A method for diagnosing breast cancer in an individual, comprising detecting in a sample isolated from the individual the presence of a breast cancer-associated protein comprising an amino acid sequence selected from the group consisting of SEQ ID NO: 3, SEQ ID NO: 4, SEQ ID NO: 5, and SEQ ID NO: 16, which if present is indicative of breast cancer in the individual.

2. The method according to claim 1, wherein the sample is a breast tissue sample.

3. The method according to claim 1, wherein the sample is a body fluid sample.

4. The method according to claim 3, wherein the body fluid sample comprises blood.

5. The method according to claim 1, wherein the breast cancer-associated protein comprises the amino acid sequence set forth in SEQ ID NO: 3.

6. The method according to claim 1, wherein the breast cancer-associated protein comprises the amino acid sequence set forth in SEQ ID NO: 4.

7. The method according to claim 1, wherein the breast cancer-associated protein comprises the amino acid sequence set forth in SEQ ID NO: 5.

8. The method according to claim 1, wherein the breast cancer-associated protein comprises the amino acid sequence set forth in SEQ ID NO: 16.

9. A method for diagnosing breast cancer in an individual, comprising detecting in a sample isolated from the individual the presence of a breast cancer-associated protein comprising an amino acid sequence selected from the group consisting of SEQ ID NO: 6, SEQ ID NO: 7, SEQ ID NO: 8, SEQ ID NO: 9, SEQ ID NO: 10, SEQ ID NO: 18, and SEQ ID NO: 20, which if present is indicative of breast cancer in the individual.

10. The method according to claim 9, wherein the sample is a breast tissue sample.

11. The method according to claim 9, wherein the sample is a body fluid sample.

12. The method according to claim 11, wherein the body fluid sample comprises blood.

13. The method according to claim 9, wherein the breast cancer-associated protein comprises the amino acid sequence set forth in SEQ ID NO: 6.

14. The method according to claim 9, wherein the breast cancer-associated protein comprises the amino acid sequence set forth in SEQ ID NO: 7.

15. The method according to claim 9, wherein the breast cancer-associated protein comprises the amino acid sequence set forth in SEQ ID NO: 8.

16. The method according to claim 9, wherein the breast cancer-associated protein comprises the amino acid sequence set forth in SEQ ID NO: 9.

17. The method according to claim 9, wherein the breast cancer-associated protein comprises the amino acid sequence set forth in SEQ ID NO: 10.

18. The method according to claim 9, wherein the breast cancer-associated protein comprises the amino acid sequence set forth in SEQ ID NO: 18.

19. The method according to claim 9, wherein the breast cancer-associated protein comprises the amino acid sequence set forth in SEQ ID NO: 20.

20. A method for detecting the presence of breast cancer in an individual, the method comprising the steps of:
   (a) contacting a sample from the individual with an antibody-based binding moiety which binds specifically to a breast cancer-associated protein to produce an antibody-breast cancer-associated protein complex, wherein the antibody-based binding moiety binds specifically to a protein comprising an amino acid sequence selected from the group consisting of SEQ ID NO: 16, SEQ ID NO: 18, and SEQ ID NO: 20; and
   (b) detecting the presence of the complex, which if present is indicative of the presence of breast cancer in the individual.

21. The method according to claim 20, wherein the sample is a tissue or body fluid sample.

22. The method of claim 20, wherein the antibody-based binding moiety is an antibody.

23. The method according to claim 22, wherein the antibody is a monoclonal antibody.

24. The method according to claim 22, wherein the antibody is labeled with a detectable label.

25. The method according to claim 24, wherein the label is selected from the group consisting of a radioactive label, a hapten label, a fluorescent label, and an enzymatic label.

* * * * *

SEQUENCE LISTING (1) GENERAL INFORMATION:

(iii) NUMBER OF SEQUENCES: 24

(2) INFORMATION FOR SEQ ID NO:1:

```
       (i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:1:

Asp Leu Ile Ser His Asp Glu Met Phe Ser Asp Ile Tyr Lys
1               5                  10

(2) INFORMATION FOR SEQ ID NO:2:

(i) SEQUENCE CHARACTERISTICS:
            (A) LENGTH: 16 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:2:

Thr Glu Gly Asn Ile Asp Asp Ser Leu Ile Gly Gly Asn Ala Ser Ala
1               5                  10                  15

(2) INFORMATION FOR SEQ ID NO:3:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:3:

Lys Ala Glu Ala Ala Ala Ser Ala Leu
1               5

(2) INFORMATION FOR SEQ ID NO:4:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:4:

Lys Phe Val Leu Met Arg
1               5

(2) INFORMATION FOR SEQ ID NO:5:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:5:

Ala Asn Ile Gln Ala Val Ser Leu Lys
1               5

(2) INFORMATION FOR SEQ ID NO:6:
```

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Ser Asp Val Val Pro Met Thr Ala Glu Asn Phe Arg
1               5                   10

(2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Ile Ile Pro Gln Phe Met Cys Gln Gly Gly Asp Phe Xaa Asn His Arg
1               5                   10                  15

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Lys Phe Asp Asp Glu Asn Phe Ile Leu Arg
1               5                   10

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

His Val Val Phe Gly Glu Val Thr Glu Gly Leu Asp Val Leu Arg
1               5                   10                  15

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Val Ile Ile Ala Asp Cys Gly Glu Tyr
1               5

(2) INFORMATION FOR SEQ ID NO:11:

(i) SEQUENCE CHARACTERISTICS:
        (A) LENGTH: 613 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..519

(xi) SEQUENCE DESCRIPTION: SEQ ID NO:11:

```
AGA TGG CCA AGC AAG GCC AGA TGG ATG CTG TTC GCA TCA TGG CAA AAG      48
Arg Trp Pro Ser Lys Ala Arg Trp Met Leu Phe Ala Ser Trp Gln Lys
 1               5                  10                  15

ACT TGG GTT GCA CCC GGC TAT GTG CGC AAG TTT GTA TTG ATG CGG GCC      96
Thr Trp Val Ala Pro Gly Tyr Val Arg Lys Phe Val Leu Met Arg Ala
             20                  25                  30

AAC ATC CAG GCT GTG TCC CTC AAG ATC CAG ACA CTC AAG TCC AAC AAC     144
Asn Ile Gln Ala Val Ser Leu Lys Ile Gln Thr Leu Lys Ser Asn Asn
         35                  40                  45

TCG ATG GCA CAA GCC ATG AAG GGT GTC ACC AAG GCC ATG GGC ACC ATG     192
Ser Met Ala Gln Ala Met Lys Gly Val Thr Lys Ala Met Gly Thr Met
 50                  55                  60

AAC AGA CAG CTG AAG TTG CCC CAG ATC CAG AAG ATC ATG ATG GAG TTT     240
Asn Arg Gln Leu Lys Leu Pro Gln Ile Gln Lys Ile Met Met Glu Phe
65                  70                  75                  80

GAG CGG CAG GCA GAG ATC ATG GAT ATG AAG GAG GAG ATG ATG AAT GAT     288
Glu Arg Gln Ala Glu Ile Met Asp Met Lys Glu Glu Met Met Asn Asp
                 85                  90                  95

GCC ATT GAT GAT GCC ATG GGT GAT GAG GAA GAT GAA GAG GAG AGT GAT     336
Ala Ile Asp Asp Ala Met Gly Asp Glu Glu Asp Glu Glu Glu Ser Asp
            100                 105                 110

GCT GTG GTG TCC CAG GTT CTG GAT GAG CTG GGA CTT AGC CTA ACA GAT     384
Ala Val Val Ser Gln Val Leu Asp Glu Leu Gly Leu Ser Leu Thr Asp
        115                 120                 125

GAG CTG TCG AAC CTC CCC TCA ACT GGG GGC TCG CTT AGT GTG GCT GCT     432
Glu Leu Ser Asn Leu Pro Ser Thr Gly Gly Ser Leu Ser Val Ala Ala
    130                 135                 140

GGT GGG AAA AAA GCA GAG GCC GCA GCC TCA GCC CTA GCT GAT GCT GAT     480
Gly Gly Lys Lys Ala Glu Ala Ala Ser Ala Leu Ala Asp Ala Asp
145                 150                 155                 160

GCA GAC CTG GAG GAA CGG CTT AAG AAC CTG CGG AGG GAC TGAGTGCCCC      529
Ala Asp Leu Glu Glu Arg Leu Lys Asn Leu Arg Arg Asp
                165                 170

TGCCACTCCG AGATAACCAG TGGATGCCCA GGATCTTTTA CCACAACCCC TCTGTAATAA   589

AAGAGATTTG ACACTAAAAA AAAA                                          613
```

(2) INFORMATION FOR SEQ ID NO:12:

(i) SEQUENCE CHARACTERISTICS:
        (A) LENGTH: 173 amino acids
        (B) TYPE: amino acid
        (D) TOPOLOGY: linear (ii) MOLECULE TYPE: protein (xi) SEQUENCE DESCRIPTION: SEQ ID NO:12:

```
Arg Trp Pro Ser Lys Ala Arg Trp Met Leu Phe Ala Ser Trp Gln Lys
 1               5                  10                  15

Thr Trp Val Ala Pro Gly Tyr Val Arg Lys Phe Val Leu Met Arg Ala
             20                  25                  30
```

-continued

```
Asn Ile Gln Ala Val Ser Leu Lys Ile Gln Thr Leu Lys Ser Asn Asn
         35                  40                  45
Ser Met Ala Gln Ala Met Lys Gly Val Thr Lys Ala Met Gly Thr Met
 50                  55                  60
Asn Arg Gln Leu Lys Leu Pro Gln Ile Gln Lys Ile Met Met Glu Phe
 65                  70                  75                  80
Glu Arg Gln Ala Glu Ile Met Asp Met Lys Glu Met Met Asn Asp
                 85                  90                  95
Ala Ile Asp Asp Ala Met Gly Asp Glu Asp Glu Glu Ser Asp
                100                 105                 110
Ala Val Val Ser Gln Val Leu Asp Glu Leu Gly Leu Ser Leu Thr Asp
                115                 120                 125
Glu Leu Ser Asn Leu Pro Ser Thr Gly Gly Ser Leu Ser Val Ala Ala
130                 135                 140
Gly Gly Lys Lys Ala Glu Ala Ala Ala Ser Ala Leu Ala Asp Ala Asp
145                 150                 155                 160
Ala Asp Leu Glu Glu Arg Leu Lys Asn Leu Arg Arg Asp
                165                 170

(2) INFORMATION FOR SEQ ID NO:13:

(i) SEQUENCE CHARACTERISTICS:
        (A) LENGTH: 121 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

Cys Gln Gly Gly Asp Phe Thr Asn His Asn Gly Thr Gly Gly Lys Ser
 1               5                  10                  15
Ile Tyr Gly Lys Lys Phe Asp Asp Glu Asn Phe Ile Leu Lys His Thr
                20                  25                  30
Gly Pro Gly Xaa Xaa Leu Ser Met Ala Asn Ser Gly Pro Lys His Gln
         35                  40                  45
Trp Leu Ser Val Leu Pro Asp Met Leu Thr Arg Gln Thr Gly Trp Asp
 50                  55                  60
Gly Gln Ala Cys Gly Val Xaa Glu Arg Phe Thr Glu Gly Leu Arg Xaa
 65                  70                  75                  80
Val Leu Arg Gln Ile Glu Ala Gln Gly Ser Lys Asp Gly Lys Pro Lys
                 85                  90                  95
Gln Lys Val Ile Ile Ala Asp Cys Gly Glu Tyr Val Leu Arg Ala Ala
                100                 105                 110
Leu Ser Leu Leu Ser Pro Ser Ala Leu
        115                 120

(2) INFORMATION FOR SEQ ID NO:14:

(i) SEQUENCE CHARACTERISTICS:
        (A) LENGTH: 141 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

Leu Arg Ser Asp Val Val Pro Met Thr Ala Glu Asn Phe Arg Cys Leu
```

```
1               5                   10                  15
Cys Thr His Glu Lys Gly Phe Gly Phe Lys Gly Ser Ser Phe His Arg
                20                  25                  30
Ile Ile Pro Gln Phe Met Cys Gln Gly Gly Asp Phe Thr Asn His Asn
                35                  40                  45
Gly Thr Gly Gly Lys Ser Ile Tyr Gly Lys Lys Phe Asp Asp Glu Asn
 50                  55                  60
Phe Ile Leu Lys His Thr Gly Pro Gly Xaa Xaa Leu Ser Met Ala Asn
 65                  70                  75                  80
Ser Gly Pro Lys His Gln Trp Leu Ser Val Leu Pro Asp Met Leu Thr
                85                  90                  95
Arg Gln Thr Gly Trp Asp Gly Gln Ala Cys Gly Val Xaa Glu Arg Phe
                100                 105                 110
Thr Glu Gly Leu Arg Xaa Val Leu Arg Gln Ile Glu Lys Gln Glu Glu
                115                 120                 125
Ser Ala Ile Thr Ser Gln Pro Arg Xaa Trp Lys Leu Thr
 130                 135                 140

(2) INFORMATION FOR SEQ ID NO:15:

(i) SEQUENCE CHARACTERISTICS:
        (A) LENGTH: 903 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 130..795
        (D) OTHER INFORMATION: /product= "BC-2"

(xi) SEQUENCE DESCRIPTION: SEQ ID NO:15:

CGGCGGCGGC GACAGGACCG AGGGGCCTTA GTTGGTGGGC AAGTCGGGGA TCCCAGAAAG        60

AGAAGCGTGA CCCGGAAGCG GAAACGGGTG TCCGTCCCAG CTCCGGCCTG CCAGTGAGCT       120

TCTACCATC ATG GAC CTA TTG TTC GGG CGC CGG AAG ACG CCA GAG GAG          168
          Met Asp Leu Leu Phe Gly Arg Arg Lys Thr Pro Glu Glu
           1               5                   10

CTA CTG CGG CAG AAC CAG AGG GCC CTG AAC CGT GCC ATG CGG GAG CTG        216
Leu Leu Arg Gln Asn Gln Arg Ala Leu Asn Arg Ala Met Arg Glu Leu
      15                  20                  25

GAC CGC GAG CGA CAG AAA CTA GAG ACC CAG GAG AAG AAA ATC ATT GCA        264
Asp Arg Glu Arg Gln Lys Leu Glu Thr Gln Glu Lys Lys Ile Ile Ala
 30                  35                  40                  45

GAC ATT AAG AAG ATG GCC AAG CAA GGC CAG ATG GAT GCT GTT CGC ATC        312
Asp Ile Lys Lys Met Ala Lys Gln Gly Gln Met Asp Ala Val Arg Ile
                 50                  55                  60

ATG GCA AAA GAC TTG GTG CGC ACC CGG CGT TAT GTG CGC AAG TTT GTA        360
Met Ala Lys Asp Leu Val Arg Thr Arg Arg Tyr Val Arg Lys Phe Val
                 65                  70                  75

TTG ATG CGG GCC AAC ATC CAG GCT GTG TCC CTC AAG ATC CAG ACA CTC        408
Leu Met Arg Ala Asn Ile Gln Ala Val Ser Leu Lys Ile Gln Thr Leu
             80                  85                  90

AAG TCC AAC AAC TCG ATG GCA CAA GCC ATG AAG GGT GTC ACC AAG GCC        456
Lys Ser Asn Asn Ser Met Ala Gln Ala Met Lys Gly Val Thr Lys Ala
     95                  100                 105

ATG GGC ACC ATG AAC AGA CAG CTG AAG TTG CCC CAG ATC CAG AAG ATC        504
Met Gly Thr Met Asn Arg Gln Leu Lys Leu Pro Gln Ile Gln Lys Ile
110                 115                 120                 125
```

```
ATG ATG GAG TTT GAG CGG CAG GCA GAG ATC ATG GAT ATG AAG GAG GAG      552
Met Met Glu Phe Glu Arg Gln Ala Glu Ile Met Asp Met Lys Glu Glu
            130                 135                 140

ATG ATG AAT GAT GCC ATT GAT GAT GCC ATG GGT GAT GAG GAA GAT GAA      600
Met Met Asn Asp Ala Ile Asp Asp Ala Met Gly Asp Glu Glu Asp Glu
            145                 150                 155

GAG GAG AGT GAT GCT GTG GTG TCC CAG GTT CTG GAT GAG CTG GGA CTT      648
Glu Glu Ser Asp Ala Val Val Ser Gln Val Leu Asp Glu Leu Gly Leu
            160                 165                 170

AGC CTA ACA GAT GAG CTG TCG AAC CTC CCC TCA ACT GGG GGC TCG CTT      696
Ser Leu Thr Asp Glu Leu Ser Asn Leu Pro Ser Thr Gly Gly Ser Leu
    175                 180                 185

AGT GTG GCT GCT GGT GGG AAA AAA GCA GAG GCC GCA GCC TCA GCC CTA      744
Ser Val Ala Ala Gly Gly Lys Lys Ala Glu Ala Ala Ala Ser Ala Leu
190                 195                 200                 205

GCT GAT GCT GAT GCA GAC CTG GAG GAA CGG CTT AAG AAC CTG CGG AGG      792
Ala Asp Ala Asp Ala Asp Leu Glu Glu Arg Leu Lys Asn Leu Arg Arg
                210                 215                 220

GAC TGAGTGCCCC TGCCACTCCG AGATAACCAG TGGATGCCCA GGATCTTTTA           845
Asp

CCACAACCCC TCTGTAATAA AAGAGATTTG ACACTAAAAA AAAAAAAAAA AAAAAAA       903

(2) INFORMATION FOR SEQ ID NO:16:

(i) SEQUENCE CHARACTERISTICS:
        (A) LENGTH: 222 amino acids
        (B) TYPE: amino acid
        (D) TOPOLOGY: linear (ii) MOLECULE TYPE: protein (xi) SEQUENCE DESCRIPTION: SEQ ID NO:16:

Met Asp Leu Leu Phe Gly Arg Arg Lys Thr Pro Glu Glu Leu Leu Arg
  1               5                  10                  15

Gln Asn Gln Arg Ala Leu Asn Arg Ala Met Arg Glu Leu Asp Arg Glu
                 20                  25                  30

Arg Gln Lys Leu Glu Thr Gln Glu Lys Lys Ile Ile Ala Asp Ile Lys
             35                  40                  45

Lys Met Ala Lys Gln Gly Gln Met Asp Ala Val Arg Ile Met Ala Lys
 50                  55                  60

Asp Leu Val Arg Thr Arg Arg Tyr Val Arg Lys Phe Val Leu Met Arg
 65                  70                  75                  80

Ala Asn Ile Gln Ala Val Ser Leu Lys Ile Gln Thr Leu Lys Ser Asn
                 85                  90                  95

Asn Ser Met Ala Gln Ala Met Lys Gly Val Thr Lys Ala Met Gly Thr
            100                 105                 110

Met Asn Arg Gln Leu Lys Leu Pro Gln Ile Gln Lys Ile Met Met Glu
            115                 120                 125

Phe Glu Arg Gln Ala Glu Ile Met Asp Met Lys Glu Met Met Asn
            130                 135                 140

Asp Ile Asp Asp Ala Met Gly Asp Glu Glu Asp Glu Glu Glu Ser
145                 150                 155                 160

Asp Ala Val Val Ser Gln Val Leu Asp Glu Leu Gly Leu Ser Leu Thr
                165                 170                 175

Asp Glu Leu Ser Asn Leu Pro Ser Thr Gly Gly Ser Leu Ser Val Ala
            180                 185                 190

Ala Gly Gly Lys Lys Ala Glu Ala Ala Ala Ser Ala Leu Ala Asp Ala
```

```
               195                 200                 205
Asp Ala Asp Leu Glu Glu Arg Leu Lys Asn Leu Arg Arg Asp
    210                 215                 220

(2) INFORMATION FOR SEQ ID NO:17:

(i) SEQUENCE CHARACTERISTICS:
        (A) LENGTH: 1331 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 61..963
        (D) OTHER INFORMATION: /product= "BC-8 (Isoform A)"

(xi) SEQUENCE DESCRIPTION: SEQ ID NO:17:

CTACTACTAC TAGGCCACGC GTCGACTAGT ACGGGGGGGG GGGGAAAGCG CGCGAGCAAG      60

ATG GCC ACC ACC AAG CGC GTC TTG TAC GTG GGT GGA CTG GCA GAG GAA      108
Met Ala Thr Thr Lys Arg Val Leu Tyr Val Gly Gly Leu Ala Glu Glu
  1               5                  10                  15

GTG GAC GAC AAA GTT CTT CAT GCT GCG TTC ATT CCT TTT GGA GAC ATC      156
Val Asp Asp Lys Val Leu His Ala Ala Phe Ile Pro Phe Gly Asp Ile
             20                  25                  30

ACA GAT ATT CAG ATT CCT CTG GAT TAT GAA ACA GAA AAG CAC CGA GGA      204
Thr Asp Ile Gln Ile Pro Leu Asp Tyr Glu Thr Glu Lys His Arg Gly
         35                  40                  45

TTT GCT TTT GTT GAA TTT GAG TTG GCA GAG GAT GCT GCA GCA GCT ATC      252
Phe Ala Phe Val Glu Phe Glu Leu Ala Glu Asp Ala Ala Ala Ala Ile
     50                  55                  60

GAC AAC ATG AAT GAA TCT GAG CTT TTT GGA CGT ACA ATT CGT GTC AAT      300
Asp Asn Met Asn Glu Ser Glu Leu Phe Gly Arg Thr Ile Arg Val Asn
 65                  70                  75                  80

TTG GCC AAA CCA ATG AGA ATT AAG GAA GGC TCT TCC AGG CCA GTT TGG      348
Leu Ala Lys Pro Met Arg Ile Lys Glu Gly Ser Ser Arg Pro Val Trp
                 85                  90                  95

TCA GAT GAT GAC TGG TTG AAG AAG TTT TCT GGG AAG ACG CTT GAA GAG      396
Ser Asp Asp Asp Trp Leu Lys Lys Phe Ser Gly Lys Thr Leu Glu Glu
            100                 105                 110

AAT AAA GAG GAA GAA GGG TCA GAG CCT CCC AAA GCA GAG ACC CAG GAG      444
Asn Lys Glu Glu Glu Gly Ser Glu Pro Pro Lys Ala Glu Thr Gln Glu
        115                 120                 125

GGA GAG CCC ATT GCT AAA AAG GCC CGC TCA AAT CCT CAG GTG TAC ATG      492
Gly Glu Pro Ile Ala Lys Lys Ala Arg Ser Asn Pro Gln Val Tyr Met
    130                 135                 140

GAC ATC AAG ATT GGG AAC AAG CCG GCT GGC CGC ATC CAG ATG CTC CTG      540
Asp Ile Lys Ile Gly Asn Lys Pro Ala Gly Arg Ile Gln Met Leu Leu
145                 150                 155                 160

CGT TCT GAT GTC GTG CCC ATG ACA GCA GAG AAT TTC CGC TGC CTG TGC      588
Arg Ser Asp Val Val Pro Met Thr Ala Glu Asn Phe Arg Cys Leu Cys
                165                 170                 175

ACT CAT GAA AAG GGC TTT GGC TTT AAG GGA AGC AGC TTC CAC CGC ATC      636
Thr His Glu Lys Gly Phe Gly Phe Lys Gly Ser Ser Phe His Arg Ile
            180                 185                 190

ATC CCC CAG TTC ATG TGC CAG GGC GGT GAT TTC ACA AAC CAC AAT GGC      684
Ile Pro Gln Phe Met Cys Gln Gly Gly Asp Phe Thr Asn His Asn Gly
        195                 200                 205

ACT GGG GGC AAG TCC ATC TAT GGG AAG AAG TTC GAT GAT GAA AAC TTT      732
Thr Gly Gly Lys Ser Ile Tyr Gly Lys Lys Phe Asp Asp Glu Asn Phe
```

```
                        210                 215                 220
ATC CTC AAG CAT ACG GGA CCA GGT CTA CTA TCC ATG GCC AAC TCT GGC       780
Ile Leu Lys His Thr Gly Pro Gly Leu Leu Ser Met Ala Asn Ser Gly
225                 230                 235                 240

CCA AAC ACC AAT GGC TCT CAG TTC TTC CTG ACA TGT GAC AAG ACA GAC       828
Pro Asn Thr Asn Gly Ser Gln Phe Phe Leu Thr Cys Asp Lys Thr Asp
                245                 250                 255

TGG CTG GAT GGC AAG CAT GTG GTG TTT GGA GAG GTC ACC GAA GGC CTA       876
Trp Leu Asp Gly Lys His Val Val Phe Gly Glu Val Thr Glu Gly Leu
            260                 265                 270

GAT GTC TTG CGG CAA ATT GAG GCC CAG GGC AGC AAG GAC GGG AAT CCA       924
Asp Val Leu Arg Gln Ile Glu Ala Gln Gly Ser Lys Asp Gly Asn Pro
        275                 280                 285

AAG CAG AAG GTG ATC ATC GCC GAC TGT GGG GAG TAC GTG TGAGGCGGCA        973
Lys Gln Lys Val Ile Ile Ala Asp Cys Gly Glu Tyr Val
    290                 295                 300
```

CTCTCTATGA TTCCCCCTCC GCTCTTGACC CTGCATATCC AGGAAGGAAC TGCCAGCCTC       1033

AGAGGAGGCA CACCGAGGGT GCCTGTTTGA AGCAAGCAGC ATTTGGGATA TGTGCCCTTC       1093

CTCAGGGTCT GCTTGGAGCA GCTCCTCTGC AGCACAGCCT GGACTATTCC CAGGCACAGC       1153

TGTGGGCCCA GGAGCCAGCT CAGGTGCTCC CCTCCACCAT GGGCAGGCTG TGCAAAAAGC       1213

CACTGGTTTT TCTCAGCATT TGCTGCTGGG CCTCTCCTGG GACTACCAGT GTGGCTCTTA       1273

CGTGTTTTCT TTGCTAAAAT AAACCCTAGT CTTAAAAAAA AAAAAAAAAA AGGCGGCC         1331

(2) INFORMATION FOR SEQ ID NO:18:

(i) SEQUENCE CHARACTERISTICS:
        (A) LENGTH: 301 amino acids
        (B) TYPE: amino acid
        (D) TOPOLOGY: linear (ii) MOLECULE TYPE: protein (xi) SEQUENCE DESCRIPTION: SEQ ID NO:18:

```
Met Ala Thr Thr Lys Arg Val Leu Tyr Val Gly Gly Leu Ala Glu Glu
1               5                   10                  15

Val Asp Asp Lys Val Leu His Ala Ala Phe Ile Pro Phe Gly Asp Ile
                20                  25                  30

Thr Asp Ile Gln Ile Pro Leu Asp Tyr Glu Thr Glu Lys His Arg Gly
            35                  40                  45

Phe Ala Phe Val Glu Phe Glu Leu Ala Glu Asp Ala Ala Ala Ala Ile
        50                  55                  60

Asp Asn Met Asn Glu Ser Glu Leu Phe Gly Arg Thr Ile Arg Val Asn
65                  70                  75                  80

Leu Ala Lys Pro Met Arg Ile Lys Glu Gly Ser Ser Arg Pro Val Trp
                85                  90                  95

Ser Asp Asp Asp Trp Leu Lys Lys Phe Ser Gly Lys Thr Leu Glu Glu
            100                 105                 110

Asn Lys Glu Glu Glu Gly Ser Glu Pro Pro Lys Ala Glu Thr Gln Glu
        115                 120                 125

Gly Glu Pro Ile Ala Lys Lys Ala Arg Ser Asn Pro Gln Val Tyr Met
    130                 135                 140

Asp Ile Lys Ile Gly Asn Lys Pro Ala Gly Arg Ile Gln Met Leu Leu
145                 150                 155                 160

Arg Ser Asp Val Val Pro Met Thr Ala Glu Asn Phe Arg Cys Leu Cys
                165                 170                 175
```

```
Thr His Glu Lys Gly Phe Gly Phe Lys Gly Ser Ser Phe His Arg Ile
        180                 185                 190

Ile Pro Gln Phe Met Cys Gln Gly Gly Asp Phe Thr Asn His Asn Gly
        195                 200                 205

Thr Gly Gly Lys Ser Ile Tyr Gly Lys Lys Phe Asp Asp Glu Asn Phe
        210                 215                 220

Ile Leu Lys His Thr Gly Pro Gly Leu Leu Ser Met Ala Asn Ser Gly
225                 230                 235                 240

Pro Asn Thr Asn Gly Ser Gln Phe Phe Leu Thr Cys Asp Lys Thr Asp
            245                 250                 255

Trp Leu Asp Gly Lys His Val Val Phe Gly Glu Val Thr Glu Gly Leu
        260                 265                 270

Asp Val Leu Arg Gln Ile Glu Ala Gln Gly Ser Lys Asp Gly Asn Pro
        275                 280                 285

Lys Gln Lys Val Ile Ile Ala Asp Cys Gly Glu Tyr Val
        290                 295                 300

(2) INFORMATION FOR SEQ ID NO:19:

(i) SEQUENCE CHARACTERISTICS:
        (A) LENGTH: 1099 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 61..948
        (D) OTHER INFORMATION: /product= "BC-8 (Isoform B)"

(xi) SEQUENCE DESCRIPTION: SEQ ID NO:19:

CTACTACTAC TAGGCCACGC GTCGACTAGT ACGGGGGGGG GGGGAAAGCG CGCGAGCAAG      60

ATG GCC ACC ACC AAG CGC GTC TTG TAC GTG GGT GGA CTG GCA GAG GAA     108
Met Ala Thr Thr Lys Arg Val Leu Tyr Val Gly Gly Leu Ala Glu Glu
 1               5                  10                  15

GTG GAC GAC AAA GTT CTT CAT GCT GCG TTC ATT CCT TTT GGA GAC ATC     156
Val Asp Asp Lys Val Leu His Ala Ala Phe Ile Pro Phe Gly Asp Ile
             20                  25                  30

ACA GAT ATT CAG ATT CCT CTG GAT TAT GAA ACA GAA AAG CAC CGA GGA     204
Thr Asp Ile Gln Ile Pro Leu Asp Tyr Glu Thr Glu Lys His Arg Gly
         35                  40                  45

TTT GCT TTT GTT GAA TTT GAG TTG GCA GAG GAT GCT GCA GCA GCT ATC     252
Phe Ala Phe Val Glu Phe Glu Leu Ala Glu Asp Ala Ala Ala Ala Ile
     50                  55                  60

GAC AAC ATG AAT GAA TCT GAG CTT TTT GGA CGT ACA ATT CGT GTC AAT     300
Asp Asn Met Asn Glu Ser Glu Leu Phe Gly Arg Thr Ile Arg Val Asn
 65                  70                  75                  80

TTG GCC AAA CCA ATG AGA ATT AAG GAA GGC TCT TCC AGG CCA GTT TGG     348
Leu Ala Lys Pro Met Arg Ile Lys Glu Gly Ser Ser Arg Pro Val Trp
                 85                  90                  95

TCA GAT GAT GAC TGG TTG AAG AAG TTT TCT GGG AAG ACG CTT GAA GAG     396
Ser Asp Asp Asp Trp Leu Lys Lys Phe Ser Gly Lys Thr Leu Glu Glu
            100                 105                 110

AAT AAA GAG GAA GAA GGG TCA GAG CCT CCC AAA GCA GAG ACC CAG GAG     444
Asn Lys Glu Glu Glu Gly Ser Glu Pro Pro Lys Ala Glu Thr Gln Glu
        115                 120                 125

GGA GAG CCC ATT GCT AAA AAG GCC CGC TCA AAT CCT CAG GTG TAC ATG     492
Gly Glu Pro Ile Ala Lys Lys Ala Arg Ser Asn Pro Gln Val Tyr Met
    130                 135                 140
```

-continued

```
GAC ATC AAG ATT GGG AAC AAG CCG GCT GGC CGC ATC CAG ATG CTC CTG          540
Asp Ile Lys Ile Gly Asn Lys Pro Ala Gly Arg Ile Gln Met Leu Leu
145                 150                 155                 160

CGT TCT GAT GTC GTG CCC ATG ACA GCA GAG AAT TTC CGC TGC CTG TGC          588
Arg Ser Asp Val Val Pro Met Thr Ala Glu Asn Phe Arg Cys Leu Cys
                165                 170                 175

ACT CAT GAA AAG GGC TTT GGC TTT AAG GGA AGC AGC TTC CAC CGC ATC          636
Thr His Glu Lys Gly Phe Gly Phe Lys Gly Ser Ser Phe His Arg Ile
            180                 185                 190

ATC CCC CAG TTC ATG TGC CAG GGC GGT GAT TTC ACA AAC CAC AAT GGC          684
Ile Pro Gln Phe Met Cys Gln Gly Gly Asp Phe Thr Asn His Asn Gly
        195                 200                 205

ACT GGG GGC AAG TCC ATC TAT GGG AAG AAG TTC GAT GAT GAA AAC TTT          732
Thr Gly Gly Lys Ser Ile Tyr Gly Lys Lys Phe Asp Asp Glu Asn Phe
    210                 215                 220

ATC CTC AAG CAT ACG GGA CCA GGT CTA CTA TCC ATG GCC AAC TCT GGC          780
Ile Leu Lys His Thr Gly Pro Gly Leu Leu Ser Met Ala Asn Ser Gly
225                 230                 235                 240

CCA AAC ACC AAT GGC TCT CAG TTC TTC CTG ACA TGT GAC AAG ACA GAC          828
Pro Asn Thr Asn Gly Ser Gln Phe Phe Leu Thr Cys Asp Lys Thr Asp
                245                 250                 255

TGG CTG GAT GGC AAG CAT GTG GTG TTT GGA GAG GTC ACC GAA GGC CTA          876
Trp Leu Asp Gly Lys His Val Val Phe Gly Glu Val Thr Glu Gly Leu
            260                 265                 270

GAT GTC TTG CGG CAA ATT GAG AAA CAA GAA GAG TCA GCA ATT ACC AGC          924
Asp Val Leu Arg Gln Ile Glu Lys Gln Glu Glu Ser Ala Ile Thr Ser
        275                 280                 285

CAG CCG AGG TCC TGG AAG CTG ACG TAGAGCTCGT GCCGACGGCA GACCTGCCGG         978
Gln Pro Arg Ser Trp Lys Leu Thr
    290                 295

CCGTGGGAGC CGTGGACGTC ATCTGCAGGG ACAGAAGGGG CAAGGTCTTT TCTGGGGTTC       1038

CTACTGTGTG CAGCTACTAT GGGGTACCAG GGTGGGGGAT GCCCTGATGA GCACATTTGT       1098

C                                                                        1099
```

(2) INFORMATION FOR SEQ ID NO:20:

(i) SEQUENCE CHARACTERISTICS:
        (A) LENGTH: 296 amino acids
        (B) TYPE: amino acid
        (D) TOPOLOGY: linear (ii) MOLECULE TYPE: protein (xi) SEQUENCE DESCRIPTION: SEQ ID NO:20:

```
Met Ala Thr Thr Lys Arg Val Leu Tyr Val Gly Gly Leu Ala Glu Glu
1               5                   10                  15

Val Asp Asp Lys Val Leu His Ala Ala Phe Ile Pro Phe Gly Asp Ile
            20                  25                  30

Thr Asp Ile Gln Ile Pro Leu Asp Tyr Glu Thr Glu Lys His Arg Gly
        35                  40                  45

Phe Ala Phe Val Glu Phe Glu Leu Ala Glu Asp Ala Ala Ala Ala Ile
    50                  55                  60

Asp Asn Met Asn Glu Ser Glu Leu Phe Gly Arg Thr Ile Arg Val Asn
65                  70                  75                  80

Leu Ala Lys Pro Met Arg Ile Lys Glu Gly Ser Ser Arg Pro Val Trp
                85                  90                  95

Ser Asp Asp Asp Trp Leu Lys Lys Phe Ser Gly Lys Thr Leu Glu Glu
                100                 105                 110
```

```
Asn Lys Glu Glu Glu Gly Ser Glu Pro Pro Lys Ala Glu Thr Gln Glu
        115                 120                 125

Gly Glu Pro Ile Ala Lys Lys Ala Arg Ser Asn Pro Gln Val Tyr Met
    130                 135                 140

Asp Ile Lys Ile Gly Asn Lys Pro Ala Gly Arg Ile Gln Met Leu Leu
145                 150                 155                 160

Arg Ser Asp Val Val Pro Met Thr Ala Glu Asn Phe Arg Cys Leu Cys
                165                 170                 175

Thr His Glu Lys Gly Phe Gly Phe Lys Gly Ser Ser Phe His Arg Ile
            180                 185                 190

Ile Pro Gln Phe Met Cys Gln Gly Gly Asp Phe Thr Asn His Asn Gly
            195                 200                 205

Thr Gly Gly Lys Ser Ile Tyr Gly Lys Lys Phe Asp Asp Glu Asn Phe
    210                 215                 220

Ile Leu Lys His Thr Gly Pro Gly Leu Leu Ser Met Ala Asn Ser Gly
225                 230                 235                 240

Pro Asn Thr Asn Gly Ser Gln Phe Phe Leu Thr Cys Asp Lys Thr Asp
                245                 250                 255

Trp Leu Asp Gly Lys His Val Val Phe Gly Glu Val Thr Glu Gly Leu
            260                 265                 270

Asp Val Leu Arg Gln Ile Glu Lys Gln Glu Glu Ser Ala Ile Thr Ser
            275                 280                 285

Gln Pro Arg Ser Trp Lys Leu Thr
    290                 295

(2) INFORMATION FOR SEQ ID NO:21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:21:

ACTTCTTCCC ATAGATGGAC TTG                                          23

(2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:22:

CGCGCGGATC CATGGCCACC ACCAAGCGC                                    29

(2) INFORMATION FOR SEQ ID NO:23:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:23:

CTGCTCGAGT GCGGCCGCTC CAAAAAGCTC AGATTC                            36

(2) INFORMATION FOR SEQ ID NO:24:
```

-continued

```
    (i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Leu Ala Asp Ala Asp Ala Asp Leu Glu Glu Arg Leu Lys Asn Leu Arg
1               5                   10                  15

Arg Asp
```